(12) United States Patent
Nakamoto et al.

(10) Patent No.: US 8,828,373 B2
(45) Date of Patent: *Sep. 9, 2014

(54) POLYALKYLENE GLYCOL DERIVATIVE AND MODIFIED BIO-RELATED SUBSTANCE

(75) Inventors: Ken-ichiro Nakamoto, Kanagawa (JP); Syunsuke Ohashi, Kanagawa (JP); Yuji Yamamoto, Tokyo (JP); Kenji Sakanoue, Kanagawa (JP); Chika Itoh, Kanagawa (JP); Tohru Yasukohchi, Kanagawa (JP)

(73) Assignee: NOF Corporation, Tokyo (JP)

( * ) Notice: Subject to any disclaimer, the term of this patent is extended or adjusted under 35 U.S.C. 154(b) by 635 days.

This patent is subject to a terminal disclaimer.

(21) Appl. No.: 11/142,683

(22) Filed: Jun. 2, 2005

(65) Prior Publication Data

US 2006/0115450 A1 Jun. 1, 2006

Related U.S. Application Data

(63) Continuation-in-part of application No. 10/716,432, filed on Nov. 20, 2003, now abandoned.

(30) Foreign Application Priority Data

Nov. 20, 2002 (JP) ............................. P. 2002-337113

(51) Int. Cl.
*A61K 31/765* (2006.01)
*C08F 283/00* (2006.01)
*C08G 65/329* (2006.01)
*C08G 65/333* (2006.01)
*C08G 65/26* (2006.01)
*A61K 47/48* (2006.01)

(52) U.S. Cl.
CPC .......... *C08G 65/2609* (2013.01); *C08G 65/329* (2013.01); *C08G 65/333* (2013.01); *A61K 47/48215* (2013.01)
USPC ....................................... 424/78.38; 525/521

(58) Field of Classification Search
CPC ................... A61K 47/48215; C08G 65/2609; C08G 65/329; C08G 65/333
USPC ................................ 424/400, 78.38; 525/521
See application file for complete search history.

(56) References Cited

U.S. PATENT DOCUMENTS

| 5,118,448 | A | 6/1992 | Cooper |
| 6,667,292 | B1 | 12/2003 | Kitabatake et al. |
| 7,851,491 | B2 | 12/2010 | Nakamoto et al. |
| 2005/0058620 | A1* | 3/2005 | Nakamoto et al. ......... 424/78.38 |
| 2005/0288490 | A1* | 12/2005 | Nakamoto et al. ............ 530/385 |
| 2006/0073113 | A1* | 4/2006 | Nakamoto et al. ......... 424/78.38 |

FOREIGN PATENT DOCUMENTS

| EP | 0043966 A1 | 6/1981 |
| JP | 2242823 A | 9/1990 |
| JP | 6-145341 A | 5/1994 |
| JP | 8-59818 A | 3/1996 |
| JP | 11-228685 A | 8/1999 |
| JP | 2000-1541 A | 1/2000 |
| JP | 2003-113241 A | 4/2003 |

OTHER PUBLICATIONS

Bhattacharya, Santanu, et al., "Synthesis of novel cationic lipids with oxyethylene spacers at the linkages between hydrocarbon chains and pseudoglyceryl backbone", Tetrahedron Letters 40, 1999, pp. 8167-8171.
Japanese Office Action dated May 28, 2012 issued in JP 2009-003472.

* cited by examiner

*Primary Examiner* — Kortney L Klinkel
(74) *Attorney, Agent, or Firm* — Sughrue Mion, PLLC

(57) ABSTRACT

A polyalkylene glycol derivative containing a compound of the formula (1):

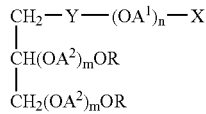 (1)

wherein R is a hydrocarbon group having 1 to 24 carbon atoms, $OA^1$ and $OA^2$ are each an oxyalkylene group having 2 to 4 carbon atoms, the groups represented by R are the same or different from each other in one molecule, the groups represented by $OA^2$ are the same or different from each other in one molecule, m is an average number of moles of the above oxyalkylene group added, m represents 10 to 1000, X represents a functional group capable of chemically reacting with a bio-related substance, and Y is a linker and represents an ether bond, an amide bond, a urethane bond, an ester bond, a secondary amino group, a carbonate bond, or an alkylene group containing these bonds, polydispersity Mw/Mn of the above polyalkylene glycol derivative in gel permeation chromatography satisfying the following relationship:

$Mw/Mn \leq 1.08$ wherein Mw represents a weight average molecular weight and Mn represents a number average molecular weight.

39 Claims, 3 Drawing Sheets

ELUTION START POINT    ELUTION END POINT

AREA-A PATTERN DIAGRAM

AREA-L PATTERN DIAGRAM

IN THE CASE THAT A MINIMUM POINT IS OBSERVED

IN THE CASE THAT A MINIMUM POINT IS NOT OBSERVED

CHROMATOGRAM PATTERN DIAGRAM

SEQUENCE LISTING

<160> NUMBER OF SEQ ID NOS: 1

<210> SEQ ID NO 1
<211> LENGTH: 24
<212> TYPE: PRT
<213> ORGANISM: Homo sapiens

<400> SEQUENCE: 1

Met Ala Pro Arg Gly Phe Ser Cys Leu Leu Leu Leu Thr Ser Glu Ile
1               5                   10                  15

Asp Leu Pro Val Lys Arg Arg Ala
            20

POLYALKYLENE GLYCOL DERIVATIVE AND MODIFIED BIO-RELATED SUBSTANCE

This is a Continuation-In-Part application which claims priority under 35 U.S.C §120 to application Ser. No. 10/716,432 filed in the United States on Nov. 20, 2003 now abandoned; the entire content of which is hereby incorporated by reference.

FIELD OF THE INVENTION

The present invention relates to a reactive polyalkylene glycol derivative, and a bio-related substance modified with the reactive polyalkylene glycol derivative.

BACKGROUND ART OF THE INVENTION

Recently, a large number of proteins, polypeptides, synthetic compounds, and compounds extracted from natural resources having physiological activity have been found out and the application thereof to pharmaceuticals has been extensively studied. However, these physiologically active substances have short half-lives in blood when they are injected to a body and hence it is difficult to obtain a sufficient pharmacological effect. This is because the physiologically active substances injected to a body are usually cleared from the body because of the filtration through glomeruli in the kidney and the uptake by macrophages in the liver, spleen, and the like. Therefore, it is attempted to improve the behavior in a body by including these physiologically active substances in liposomes or polymer micelles or increasing their molecular weight through chemical modification with polyethylene glycol which is an amphiphatic polymer. Polyethylene glycol exhibits a low interaction with the other bio-components owing to its steric repulsion effect and as a result, proteins and polypeptides such as enzymes modified with polyethylene glycol exhibit an effect of avoiding the filtration through glomeruli in the kidney and bio-reactions such as immunoreaction, so that they achieve half-lives in blood longer than those of unmodified substances. Moreover, they also have decreased toxicity and antigpnicity and further exhibit an effect of enhancing the solubility of a sparingly water-soluble compound having a high hydrophobicity.

In the case of modifying a physiologically active substance with a linear polyethylene glycol, it is known that modification effects such as half-lives in blood is enhanced as molecular weight of the polyethylene glycol increases. Therefore, synthesis of a reactive polyethylene glycol derivative having a higher molecular weight has been investigated. However, when a starting methoxypolyethylene glycol is synthesized by addition polymerization of ethylene oxide, particularly in the case that a high-molecular-weight one is intended to obtain, there is increased side-reaction such as vinyl etherification and impurities such as compounds having a two-time molecular weight derived from an initiator. Accordingly, it is difficult to obtain a methoxypolyethylene glycol having a high purity and a high molecular weight. As a result, it is difficult to obtain a reactive polyalkylene glycol derivative having a high purity and a high molecular weight, which is suitable for modification of pharmaceuticals.

Moreover, when a peptide or drug is modified with many polyethylene glycol molecules for obtaining a sufficient effect of the modification with polyethylene glycol, the active site of the peptide or drug is blocked and hence there may arise problems that its own function and efficacy cannot be exhibited sufficiently and enough solubility in water cannot be obtained.

For solving such problems, an attempt to solve such problems using a branched polyethylene glycol derivative has been made. By using a branched one, it becomes possible to introduce two highly pure polyethylene glycol chains per one modifying point and hence modification with a polyethylene glycol chain having a high molecular weight is enabled. Moreover, it becomes possible to cover larger surface of a physiologically active substance with a polyethylene glycol chain. Furthermore, it becomes possible to reduce modification points as compared with the case of modification with a linear one, which enables inhibition of decrease in activity of the physiologically active substance.

JP-B-61-42558 proposes.a polyethylene glycol-modified L-asparaginase. Cyanuric chloride as a starting material for a branched reactive polyethylene glycol derivative used in the publication has three reactive sites and hence it is difficult to introduce two polyethylene glycol chains thereinto selectively. Accordingly, it is difficult to synthesize a highly pure polyethylene glycol-modified L-asparaginase.

Also, JP-A-10-67800 proposes a polyethylene glycol-modified interferon α. The branched reactive polyethylene glycol derivative used in the publication has lysine as a skeleton, wherein methoxypolyethylene glycols are combined with two amino groups of the lysine and then the carboxyl residue is converted into a succinimide ester group. In the case of the branched polyethylene glycol having a lysine skeleton, a reactive functional group is present near to the lysine skeleton and hence there is a possibility that conversion of the reaction with a physiologically active substance decreases due to steric hindrance of the own polyethylene glycol chains. Particularly, in the case that a site to be modified is present inside the polypeptide, there is a possibility that reaction is difficult to proceed in a polyethylene glycol derivative wherein a reactive group is present near to the skeleton.

Accordingly, it is desired to develop a highly reactive branched polyalkylene glycol derivative which solves the problems of these conventional polyethylene glycol derivatives, and a modified bio-related substance.

SUMMARY OF THE INVENTION

A first object of the invention is to provide a polyalkylene glycol derivative having polyalkylene glycol chains at the 2- and 3-positions of the glycerin skeleton and having a reactive group capable of being combined with a bio-related substance at the 1-position through a polyalkylene glycol chain.

A second object of the invention is to provide a bio-related substance modified with a branched polyalkylene glycol derivative.

As a result of extensive studies for solving the above problems, the present inventors have found a novel branched polyalkylene glycol derivative and a novel bio-related substance modified with a branched polyalkylene glycol derivative, and thus accomplished the invention.

Namely, the invention relates to a polyalkylene glycol derivative comprising a compound of the formula (1):

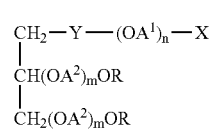

(1)

wherein R is a hydrocarbon group having 1 to 24 carbon atoms, $OA^1$ and $OA^2$ are each an oxyalkylene group having 2 to 4 carbon atoms, the groups represented by R are the same or different from each other in one molecule, the groups represented by $OA^2$ are the same or different from each other in one molecule, m is an average number of moles of the above oxyalkylene group added, m represents 10 to 1000, X represents a functional group capable of chemically reacting with a bio-related substance, and Y is a linker and represents an ether bond, an amide bond, a urethane bond, an ester bond, a secondary amino group, a carbonate bond, or an alkylene group containing these bonds, polydispersity Mw/Mn of the above polyalkylene glycol derivative in gel permeation chromatography satisfying the following relationship:

Mw/Mn≤1.08 wherein Mw represents a weight average molecular weight and Mn represents a number average molecular weight.

The branched polyalkylene glycol derivative of the invention can provide a polyalkylene glycol derivative having polyalkylene glycol chains at the 2- and 3-positions of the glycerin skeleton and having a reactive group capable of being combined with a bio-related substance at the 1-position through a polyalkylene glycol chain. Moreover, the derivative can provide a bio-related substance modified with a branched polyalkylene glycol derivative. Since the polyethylene glycol derivative of the invention has a polyalkylene glycol chain as a spacer between the glycerin skeleton and the reactive group, it is expected to show reactivity equal to that of a linear polyethylene glycol derivative. Moreover, steric hindrance owing to the own polyalkylene glycol chains is small as compared with the case of conventional branched polyethylene glycol derivatives wherein a reactive functional group is present at the joint of the polyalkylene glycol chain. Furthermore, at the reaction with a polypeptide, since chain length of the polyalkylene glycol chain as a spacer can be adjusted according to the kind of the polypeptide, it becomes possible to modify functional groups present even inside the polypeptide, so that improvement of conversion can be expected.

DETAILED DESCRIPTION OF THE INVENTION

Figure 1:
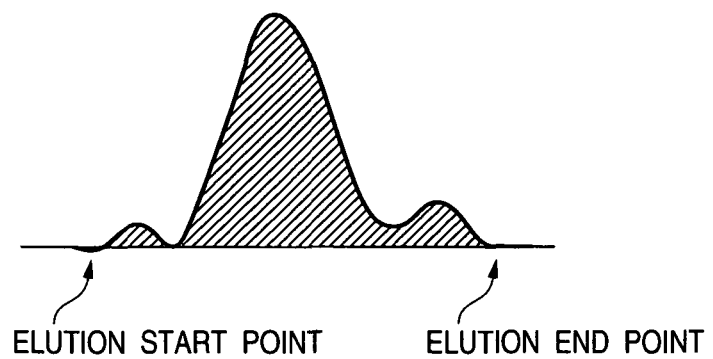
FIG. 1 is a model chart of a chromatogram obtained by gel permeation chromatography of a polyalkylene glycol derivative.

The polyalkylene glycol derivative of the present invention is represented by the formula (1):

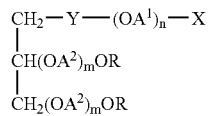

(1)

wherein R is a hydrocarbon group having 1 to 24 carbon atoms, $OA^1$ and $OA^2$ are each an oxyalkylene group having 2 to 4 carbon atoms, the groups represented by R are the same or different from each other in one molecule, the groups represented by $OA^2$ are the same or different from each other in one molecule, m is an average number of moles of the above oxyalkylene group added, m represents 10 to 1000, X represents a functional group capable of chemically reacting with a bio-related substance, and Y is a linker and represents an ether bond, an amide bond, a urethane bond, an ester bond, a secondary amino group, a carbonate bond, or an alkylene group containing these bonds, polydispersity Mw/Mn of the above polyalkylene glycol derivative in gel permeation chromatography satisfying the following relationship:

Mw/Mn≤1.08 wherein Mw represents a weight average molecular weight and Mn represents a number average molecular weight.

R in the formula (1) is a hydrocarbon group having 1 to 24 carbon atoms and specific hydrocarbon groups include hydrocarbon groups such as a methyl group, an ethyl group, a propyl group, an isopropyl group, a butyl group, a tert-butyl group, a pentyl group, an isopentyl group, a hexyl group, a heptyl group, a 2-ethylhexyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, an oleyl group, a nonadecyl group, an eicosyl group, a heneicosyl group, docosyl group, a tricosyl group, a tetracosyl group, a benzyl group, a cresyl group, a butylphenyl group, and a dodecylphenyl group. The hydrocarbon group is preferably a hydrocarbon group having 1 to 10 carbon atoms, more preferably a methyl group or an ethyl group, further preferably a methyl group. R may be the same or different from each other in one molecule.

$OA^1$ and $OA^2$ each represents an oxyalkylene group having 2 to 4 carbon atoms. Specifically, it includes an oxyethylene group, an oxypropylene group, an oxytrimethylene group, an oxy-1-ethylethylene group, an oxy-1,2-dimethylethylene group, and an oxytetramethylene group. The oxyalkylene groups may be the same or different from each other and may be added randomly or block-wise. In general, the fewer the carbon atoms are, the higher the hydrophilicity is. The group is preferably an oxyethylene group or an oxypropylene group, more preferably an oxyethylene group. $OA^2$ may be the same or different from each other in one molecule.

m and n each is an average number of moles of the oxyalkylene group added. m is 10 to 1000, preferably 50 to 1000, more preferably 100 to 1000, most preferably 200 to 1000. n is 1 to 1000, preferably 1 to 800, more preferably 10 to 800. In a preferable embodiment, n is preferably 10 to 100 and in another preferable embodiment, n is preferably 150 to 800.

Y is a linker between the glycerin skeleton and the polyoxyalkylene chain and represents an ether bond, an amide bond, a urethane bond, an ester bond, a secondary amino group, a carbonate bond, or an alkylene group containing these bonds. More preferable is an ether bond, an amide bond, a urethane bond, or an alkylene group containing these bonds. Further preferably, there are mentioned structures such as (z3), (z4), and (z5) to be described below.

X is not particularly limited as far as it is a functional group capable of forming a chemical bond with a bio-related substance. In a preferable embodiment, X is a group represented by the group (I):

Group (I)

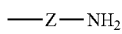  (a)

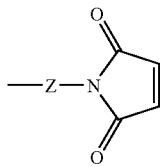  (b)

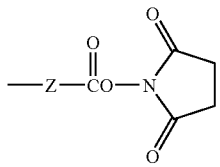  (c)

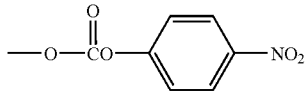  (d)

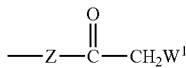  (e)

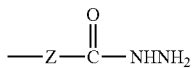  (f)

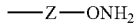  (g)

—Z—ONH$_2$  (h)

—Z—COOH  (i)

—Z—SH  (j)

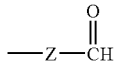

The groups represented by (c), (d), (h), and (j) are preferable in the case of reaction with an amino group of the bio-related substance, the groups represented by (b), (c), (d), (e), (h), (i), and (j) in the case of reaction with a mercapto group of the bio-related substance, the group represented by (i) in the case of reaction with an unsaturated bond of the bio-related substance, and the groups represented by (a) and (i) in the case of reaction with a carboxyl group of the bio-related substance. Moreover, the groups represented by (a), (f), (g), and (i) are preferable in the case of reaction with an aldehyde group of the bio-related substance. In the case that the bio-related substance does not have an amino group, a mercapto group, an unsaturated bond, a carboxyl group, or an aldehyde group, these groups may be suitably introduced thereto.

Z in the group (I) is a linker between the reactive functional group and the polyoxyalkylene chain and is not particularly limited as far as it is a covalent bond but preferably includes an alkylene group alone or an alkylene group containing an ester bond, a urethane bond, an amide bond, an ether bond, a carbonate bond, or a secondary amino group. Preferable alkylene group includes a methylene group, an ethylene group, a trimethylene group, a propylene group, an isopropylene group, a tetramethylene group, a butylene group, an isobutylene group, a pentamethylene group, and a hexamethylene group. More preferable is a structure of the following (z1). Further preferable as an alkylene group containing an ester bond is a structure of the following (z2). More preferable as an alkylene group containing an amide bond is a structure of the following (z3). A structure of the following (z4), (z7), or (z8) is more preferable as an alkylene group containing an ether bond. More preferable as an alkylene group containing a urethane bond is a structure of the following (z5). A structure of the following (z6) is more preferable as an alkylene group containing a secondary amino group. In each formula, s is an integer of 1 to 6, preferably an integer of 1 to 5.

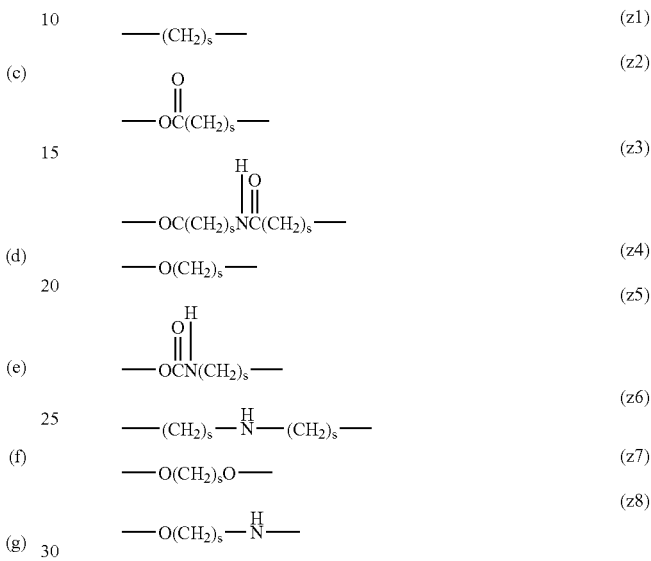

$W^1$ in the group (I) is a halogen atom selected from Cl, Br, and I, and preferable is a case of I.

FIG. 1 is a model chart of a chromatogram obtained by gel permeation chromatography of a polyalkylene glycol derivative.

In the polyalkylene glycol derivative of the formula (1), polydispersity Mw/Mn in gel permeation chromatography indicates polydispersity Mw/Mn in the whole peaks from elution start point to elution end point and satisfies a relationship:

Mw/Mn≤1.08.

More preferable is the case wherein it satisfies a relationship:

Mw/Mn≤1.07.

Further preferable is the case wherein it satisfies a relationship:

Mw/Mn≤1.06.

The case that Mw/Mn is larger than 1.08 means that high-molecular-weight impurities and low-molecular-weight impurities are present in large amounts and when a bio-related substance is combined, physical properties becomes heterogeneous, so that the product is not preferable as a pharmaceutical.

In the invention, at gel permeation chromatography, LC10AVP was employed as a GPC system and measurement was carried out under the following conditions:

developing solvent: DMF (containing 10 mM lithium bromide); flow rate: 0.7 ml/min; column: PLgel MIXED-D two columns; column temperature: 65° C.; detector: RI (manufactured by shodex); sample amount: 1 mg/mL, 100 μl.

Moreover, at analysis of an aldehyde compound, since an associate is formed under the above conditions and thus it is difficult to conduct correct measurement of molecular weight distribution, measurement was carried out under the following conditions:

system: Alliance2695 (Nihon Waters K.K.); developing solvent: 100 mM sodium acetate buffer solution (pH=5.2, containing 0.02% $NaN_3$); flow rate: 0.5 mv/min; column: Ultlahydrogel500+Ultlahydrogel250 2 columns; column temperature: 30° C.; detector: RI; sample amount: 5 mg/mL, 20 μl.

Figure 2:
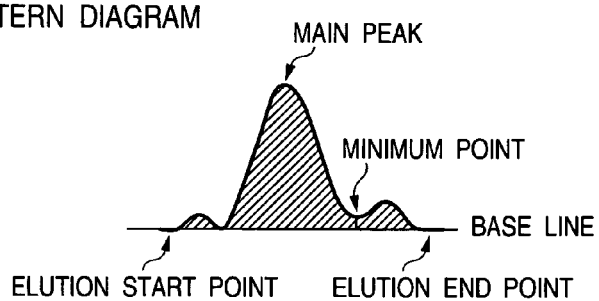
FIG. 2 is a model chart of a chromatogram obtained by gel permeation chromatography of a polyalkylene glycol derivative.
Figure 2:
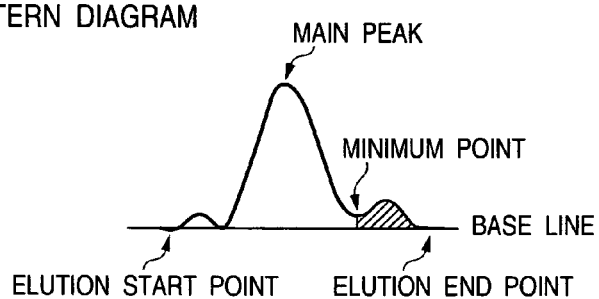
Figure 2:
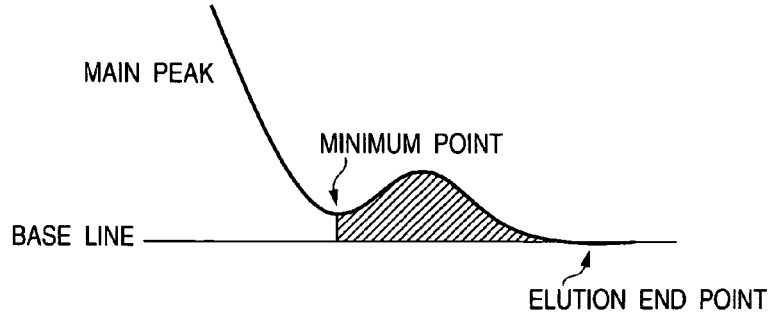
Figure 2:
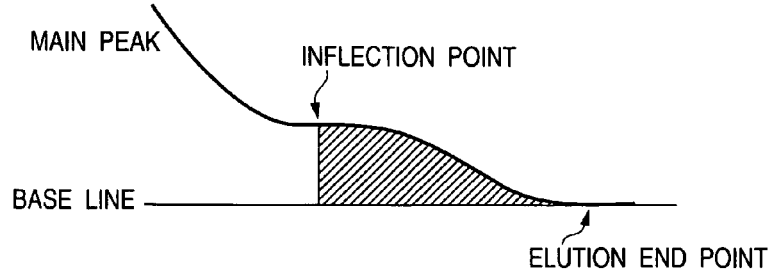

FIG. 2 is a model chart of a chromatogram obtained by gel permeation chromatography of a polyalkylene glycol derivative.

In the polyalkylene glycol derivative of the formula (1), the low-molecular-weight impurities (%) is represented by (Area-L/Area-A)×100 where a peak showing a maximum point of refractive index is regarded as a main peak among peaks excluding peaks attributable to the developing solvent and the like used and pseudo peaks owing to fluctuation of base line originated from the columns and apparatus used, a line connecting an elution start point and an elution end point of a chromatogram is used as a base line, a total peak area on and above the base line is defined as Area-A, and a peak area from a minimum point between a peak top of the main peak and a peak top of a peak to be observed next to the main peak to the elution end point is defined as Area-L. In the case that any minimum point between the peaks is not observed, a peak area from an inflection point to be first observed starting from the peak top of the main peak to the elution end point is defined as Area-L.

In the polyalkylene glycol derivative of the formula (1) of the invention, Area-A and Area-L preferably satisfy a relationship:

(Area-L/Area-A)×100≤8(%), more preferably satisfy a relationship:

(Area-L/Area-A)×100≤6(%), further preferably satisfy a relationship:

(Area-L/Area-A)×100≤5(%).

The case that (Area-L/Area-A)×100 is larger than 8(%) means that low-molecular-weight impurities are present in a large amount and, when a bio-related substance is combined, physical properties becomes heterogeneous, so that the product is not preferable as a pharmaceutical.

The modified bio-related substance of the invention represents a combined product of the compound of the formula (1) with a bio-related substance.

The "bio-related substance" according to the invention means a substance relating to a body. The substances relating to a body include the following.

(1) Animal Cell-Constituting Materials such as Phospholipids, Glycolipids, and Glycoproteins The animal cell-constituting materials are components constituting cell membranes or the like and the kind is not particularly limited but examples thereof include phospholipids, glycolipids, and glycoproteins. Examples of more specific phospholipids include phosphatidic acid, phosphatidylcholine, phosphatidylethanolamine, cardiolipin, phosphatidylserine, and phosphatidylinositol. In addition, lyso isomers thereof are also included. These phospholipids may be those derived from natural products such as egg yolk or soybean or may be synthesized products. The composition of fatty acids is not particularly limited but may include fatty acids having 12 to 22 carbon atoms. These fatty acids may be saturated fatty acids or may be those containing an unsaturated bond. Examples of more specific glycolipids include ceramides, cerebrosides, sphingosines, gangliosides, and glyceroglycolipids. In addition, fatty acids, monoglycerides, diglycerides, cholesterols, and bile acid are also included.

(2) Body Fluid-Constituting Substances such as Blood, Lymph, and Bone Marrow Liquid The body fluid-constituting substances mean fluid components existing inside and outside cells and the kind is not particularly limited but examples thereof include blood, lymph, and bone marrow liquid. Examples of more specific body fluid-constituting components include hemoglobin, albumin, and blood coagulation factors.

(3) Physiologically Active Substances such as Vitamins, Neurotransmitters, Proteins, Polypeptides, and Drugs The physiologically active substances mean components controlling body functions and the kind is not particularly limited but examples thereof include vitamins, neurotransmitters, proteins, polypeptides, and drugs.

Examples of more specific vitamins include vitamin A, vitamin B, vitamin C, vitamin D, vitamin E, and vitamin K.

Examples of more specific neurotransmitters include adrenalin, noradrenalin, dopamine, acetylcholine, GABA, glutamic acid, and aspartic acid.

Examples of more specific proteins and polypeptides include the following. Hormones such as neurohypophysial hormone, thyroid hormone, male sex hormone, female sex hormone, and adrenal cortex hormone. Serum proteins such as hemoglobin and blood factors. Immunoglobulins such as IgG, IgE, IgM, IgA, and IgD. Cytokines and fragments thereof, such as interleukins (IL-1, IL-2, IL-3, IL-4, IL-5, IL-6, IL-7, IL-8, IL-9, IL-10, IL-11 and IL-12 subtypes), interferons (−α, −β, −γ), granulocyte-colony stimulating factors (α and β types), macrophage-colony stimulating factor, granulocyte-macrophage colony stimulating factor, platelet-derived growth factor, phospholipase-activating protein, insulin, glucagon, lectin, ricin, tumor necrosis factor, epidermal growth factor, transforming growth factors (−α, −β), fibroblast growth factor, hepatocyte growth factor, vascular endothelial growth factor, nerve growth factor, bone growth factor, insulin-like growth factor, heparin binding growth factor, tumor growth factor, glial cell line-derived neurotrophic factor, macrophage differentiating factor, differentiation-inducing factor, leukemia inhibitory factor, amphiregurin, somatomedin, erythropoietin, hemopoietin, thrombopoietin, and calcitonin. Enzymes such as proteolytic enzymes, oxidoreductases, transferases, hydrolases, lyases, isomerases, ligases, asparaginases, arginases, arginine deaminases, adenosine deaminases, superoxide dismutases, endotoxinases, catalases, chymotrypsin, lipases, uricases, elastases, streptokinases, urokinases, prourokinases, adenosine diphosphatases, tyrosinases, bilirubin oxidases, glucose oxidases, glucodases, glactosidases, glucocerebrosidases, and glucouronidases. Monoclonal and polyclonal antibodies and fragments thereof. Polyamino acids such as poly-L-lysine and poly-D-lysine. Vaccines such as hepatitis B vaccine, malaria vaccine, melanoma vaccine, and HIV-1 vaccine, and antigens. In addition, glycoproteins are also included. Furthermore, also included are structurally similar substances having physiological activity similar to that of these physiologically active substances.

Moreover, these proteins and polypeptides may be isolated from natural sources thereof or cells subjected to genetic engineering or may be produced via various synthetic processes.

The drugs are not particularly limited but more preferably include anticancer agents and antifungal agents.

More specific anticancer agents are not particularly limited but, for example, include paclitaxel, adriamycin, doxorubicin, cisplatin, daunomycin, mitomycin, vincristine, epirubicin, methotrexate, 5-fluorouracil, aclacinomycin, idamycin, bleomycin, pirarubicin, peplomycin, vancomycin, and camptothecine.

Specific antifungal agents are not particularly limited but, for example, include amphotericin B, nystatin, flucytosine, miconazole, fluconazole, itraconazole, ketoconazole, and peptide antifungal agents.

Moreover, these physiologically active substances also include flavonoids, terpenoids, carotenoids, saponins, steroids, quinones, anthraquinones, xanthones, coumarins, alkaloids, porphyrins, and polyphenols, which possess, for example, antioxidant action, PAF inhibitory action, antiinflammatory action, and antifungal action.

The number of modifications with the polyalkylene glycol derivative to the bio-related substance is not particularly limited but is preferably 1 to 100, more preferably 1 to 20.

Tables 1 and 2 show relation between a residual group T of the above bio-related substance and a functional group X which forms a chemical bond with the residual group T.

TABLE 1

| X group | Reactive group of physiologically active substance | | | | |
|---|---|---|---|---|---|
| | T—NH$_2$ (amino group) | T—SH (Mercapto group) | T=/ (Unsaturated bond) | T—C(=O)—OH (Carboxyl group) | T—C(=O)—H (Aldehyde group) |
| (a) —Z—NH$_2$ | | | | —Z—NH—C(=O)—T (Amide) | —Z—N=CH—T (Schiff base); —Z—NH—CH$_2$—T (secondary amine) |
| (b) —Z—N(maleimide) | | —Z—N(succinimide)—S—T (sulfide) | | | |
| (c) —Z—CO—O—N(succinimide) | —Z—C(=O)—NH—T (amide) | —Z—C(=O)—S—T (thioester) | | | |
| (d) —O—CO—O—C$_6$H$_4$—NO$_2$ | —O—C(=O)—NH—T (urethane) | —O—C(=O)—S—T (thiocarbonate) | | | |
| (e) —Z—C(=O)—CH$_2$W$^1$ | | —Z—C(=O)—CH$_2$—S—T (sulfide) | | | |

TABLE 2

| X group | Reactive group of physiologically active substance | | | | |
|---|---|---|---|---|---|
| | T—NH$_2$ (Amino group) | T—SH (Mercapto group) | T=/ (Unsaturated bond) | T—C(=O)—OH (Carboxyl group) | T—C(=O)—H (Aldehyde group) |
| (f) —Z—C(=O)—NHNH$_2$ | | | | | —Z—C(=O)—NHN=CH—T (hydrazone) |

TABLE 2-continued

| | Reactive group of physiologically active substance | | | | |
|---|---|---|---|---|---|
| X group | T—NH$_2$ (Amino group) | T—SH (Mercapto group) | T= (Unsaturated bond) | T—C(=O)—OH (Carboxyl group) | T—C(=O)—H (Aldehyde group) |
| (g) —Z—ONH$_2$ | | | | | —Z—ON=CH—T (oxime) |
| (h) —Z—COOH | —Z—C(=O)—N(H)—T (amide) | —Z—C(=O)—S—T (thioester) | | | |
| (i) —Z—SH | | —Z—S—S—T (disulfide) | —Z—S—C(T)— (sulfide) | —Z—S—C(=O)—T (thioester) | —Z—S\C(H)(—Z—S)—T (thioacetal) |
| (j) —Z—CH(=O) | —Z—C(H)=N—T (Schiff base); —Z—CH$_2$—N(H)—T (secondary amine) | —Z—C(H)(S—T)(S—T) (thioacetal) | | | |

As is apparent from the tables, the functional group X in the polyalkylene glycol derivative of the invention and the bio-related substance are combined by, for example, an amide bond, a secondary amino group, a urethane bond, a thioester bond, a sulfide bond, a disulfide bond, a thibcarbonkate bond, an oxime, a hydrazone, or a thioacetal bond.

The modified bio-related substances of the invention can be produced as follows.

(Case of Reacting an Amino Group of a Bio-Related Substance with a Polyalkylene Glycol Derivative of the Invention)

In the case of the modification with an amino group of a bio-related substance, the compounds (c), (d), (h), and (j) of the invention are used. More preferably, (c), (d), and (j) are used. At the reaction, the compounds (c), (d), (h), and (j) of the invention may be reacted in a ratio of equimolar or more to the bio-related substance. The reaction solvent is not particularly limited as far as it does not participate in the reaction, but in the case of reacting a protein or polypeptide, preferable solvents include buffer solutions such as phosphate buffer solutions, borate buffer solutions, Tris-acid buffer solutions, acetate buffer solutions, and carbonate buffer solutions. Furthermore, an organic solvent which does not deactivate the protein or polypeptide and does not participate in the reaction, such as acetonitrile, dimethyl sulfoxide, dimethylformamide, or dimethylacetamide, may be added. In the case of reacting an anticancer agent, antifungal agent, or phospholipid, preferable solvents include, in addition to the above buffer solutions, toluene, benzene, xylene, acetonitrile, ethyl acetate, diethyl ether, t-butyl methyl ether, tetrahydrofuran, chloroform, methylene dichloride, dimethyl sulfoxide, dimethylformanide, dimethylacetamide, water, methanol, ethanol, n-propanol, 2-propanol, and n-butanol. Also, the solvent need not be used. The order of adding the polyalkylene glycol derivative of the invention and the bio-related substance is optional. The reaction temperature is not particularly limited as far as it does not deactivate the bio-related substance, but the temperature is preferably 0 to 40° C. in the case of reacting a protein or polypeptide and is preferably −20 to 150° C. in the case of reacting an anticancer agent, antifungal agent, or phospholipid. The reaction time is preferably 0.5 to 72 hours, more preferably 1 to 24 hours. At the reaction, a condensing agent such as N,N'-dicyclohexylcarbodiimide (DCC) or 1-ethyl-3-(3-dimethylaminopropyl)carbodiimide hydrochloride (EDC) may be used. In the case that a Schiff base is formed by the reaction, it may be subjected to reduction treatment using a reducing agent such as sodium cyanoborohydride. A covalent bond is formed between the bio-related substance and the polyalkylene glycol derivative of the invention by carrying out the reaction. An amide bond is formed in the case of using (c) or (h), and a urethane bond is formed in the case of using (d). A Schiff base is formed in the case of using (j) and the Schiff base is reduced to form a secondary amino group. After completion of the reaction, the product may be purified by a purifying means such as dialysis, salting-out, ultrafiltration, ion-exchange chromatography, electrophoresis, extraction, recrystallization, adsorption treatment, reprecipitation, column chromatography, or supercritical extraction.

(Case of Reacting a Mercapto Group of a Bio-Related Substance with a Polyalkylene Glycol Derivative of the Invention)

In the case of the modification with a mercapto group of a bio-related substance, the polyalkylene glycol derivatives of the invention (b), (c), (d), (e), (h), (i), and (j) of the invention are used. More preferably, (b) and (e) are used. The reaction solvent, reaction conditions, and the like are the same as in the case of using an amino group. At the reaction, a radical initiator such as iodine or AIBN may be used. A covalent bond is formed between the bio-related substance and the polyalkylene glycol derivative of the invention by carrying out the reaction, and a thioether bond is formed in the case of using (c) or (h), a thiocarbonate bond in the case of using (d), a disulfide bond in the case of using (i), a sulfide bond in the case of using (b) or (e), and a thioacetal bond is formed in the case of using (j).

(Case of Reacting an Unsaturated Bond of a Bio-Related Substance with a Polyalkylene Glycol Derivative of the Invention)

In the case of the modification with an unsaturated bond of a bio-related substance, the polyalkylene glycol derivative (i) of the invention is used. The reaction solvent, reaction conditions, and the like are the same as in the case of using an amino group. At the reaction, a radical initiator such as iodine or AIBN may be used. A sulfide bond is formed between the bio-related substance and the polyalkylene glycol derivative of the invention by carrying out the reaction.

(Case of Reacting a Carboxyl Group of a Bio-Related Substance with a Polyalkylene Glycol Derivative of the Invention)

In the case of the modification with a carboxyl group of a bio-related substance, the polyalkylene glycol derivative of the invention (a) or (i) of the invention is used. The reaction solvent, reaction conditions, and the like are the same as in the case of using an amino group. At the reaction, a condensing agent such as DCC or EDC may be optionally used. A covalent bond is formed between the bio-related substance and the polyalkylene glycol derivative of the invention by carrying out the reaction, and a thioester bond is formed in the case of using (i) and an amide bond in the case of using (a).

(Case of Reacting an Aldehyde Group of a Bio-Related Substance with a Polyalkylene Glycol Derivative of the Invention)

In the case of the modification with an aldehyde group of a bio-related substance, the polyalkylene glycol derivative of the invention (a), (f), (g), or (i) of the invention is used. The reaction solvent, reaction conditions, and the like are the same as in the case of using an amino group. In the case that a Schiff base is formed, it may be subjected to reduction treatment using a reducing agent such as sodium cyanoborohydride. A thioacetal bond is formed in the case of using (i), a secondary amino group in the case of using (a), an oxime in the case of using (g), and a hydrazone bond in the case of using (f).

Moreover, in the case that a bio-related substance does not have any of an amino group, a mercapto group, an unsaturated bond, a carboxyl group, and an aldehyde group, the bio-related substance can be modified by introducing a reactive group suitably into the bio-related substance and using a polyalkylene glycol derivative of the invention.

The following will describe a process for synthesizing the reactive polyalkylene glycol derivative of the invention.

(Process for Synthesizing the Polyalkylene Glycol Derivative wherein X is a Hydroxyl Group, which is an Intermediate)

The polyalkylene glycol derivatives of the formula (1) wherein X is hydroxyl group of the invention can be, for example, produced as follows. After the primary hydroxyl group residue of 2,2-dimethyl-1,3-dioxolane-4-methanol is protected with a benzyl group, the cyclic acetal structure is deprotected under an acidic condition to obtain the following general formula (pa). An alkylene oxide is polymerized in an amount of 10 to 1000 mol to the newly formed two hydroxyl groups to obtain the following general formula (pb). Then, the terminal ends are alkyl-etherified to obtain the following general formula (pc). Thereafter, the benzyl group is deprotected and thereby, the following general formula (p) can be obtained. An alkylene oxide is polymerized in an amount of 1 to 1000 mol to the hydroxyl group of the resulting compound (p) and thereby, the following general formula (pd) wherein Y is an alkylene group containing an ether bond and X is a hydroxyl group in the formula (1) can be obtained. Moreover, for example, compounds represented by the following formulae (pe1), (pf1), (pg1), and (ph1) wherein Y is an alkylene group containing a urethane bond, an amide bond, or an ester bond and X is a hydroxyl group in the formula (1) can be obtained by synthesizing compounds represented by the following formulae (pe), (pf), (pg), and (ph) and reacting the compounds with a heterogeneous polyalkylene glycol represented by the following formula (pi):

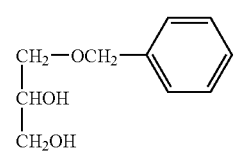
(pa)
CH$_2$—OCH$_2$—
|
CHOH
|
CH$_2$OH

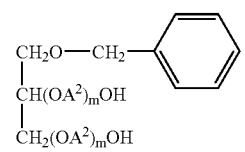
(pb)
CH$_2$O—CH$_2$—
|
CH(OA$^2$)$_m$OH
|
CH$_2$(OA$^2$)$_m$OH

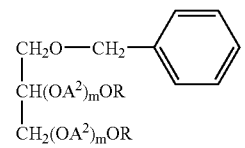
(pc)
CH$_2$O—CH$_2$—
|
CH(OA$^2$)$_m$OR
|
CH$_2$(OA$^2$)$_m$OR (p)
CH$_2$OH
|
CH(OA$^2$)$_m$OR
|
CH$_2$(OA$^2$)$_m$OR (pd)
CH$_2$(OA$^1$)$_n$OH
|
CH(OA$^2$)$_m$OR
|
CH$_2$(OA$^2$)$_m$OR

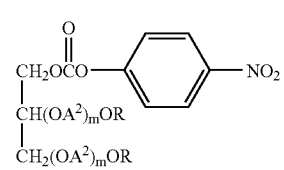
(pe)
CH$_2$OCO—⟨⟩—NO$_2$
|
CH(OA$^2$)$_m$OR
|
CH$_2$(OA$^2$)$_m$OR

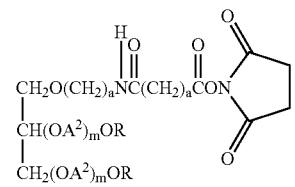
(pf)
CH$_2$O(CH$_2$)$_a$NC(CH$_2$)$_a$CON
|
CH(OA$^2$)$_m$OR
|
CH$_2$(OA$^2$)$_m$OR

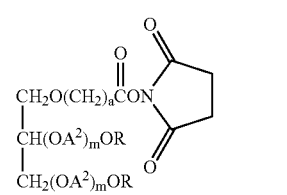
(pg)
CH$_2$O(CH$_2$)$_a$CON
|
CH(OA$^2$)$_m$OR
|
CH$_2$(OA$^2$)$_m$OR -continued

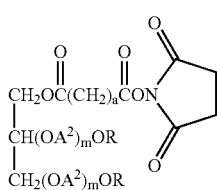
(ph)

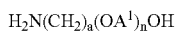
(pi)

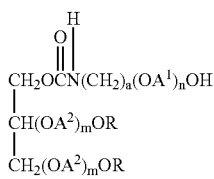
(pe1)

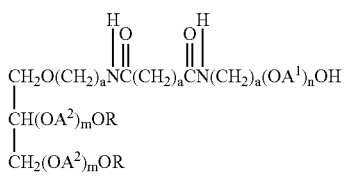
(pf1)

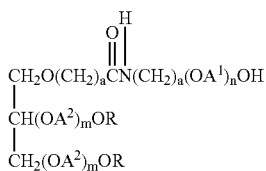
(pg1)

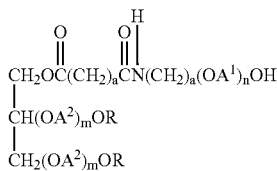
(ph1)

wherein a represents an integer of 1 to 6 and may be the same or different from each other; a is more preferably an integer of 2 to 5; and R, $OA^1$, $OA^2$, m, and n are the same as mentioned above.

As above, a highly pure branched polyalkylene glycol derivative (p) can be produced in high yields in an industrially suitable manner by using the technology of the protective reaction and the alkylene oxide-addition polymerization reaction. Moreover, by carrying out an alkylene oxide-addition polymerization reaction onto the hydroxyl group at the 1-position of the glycerin skeleton, there can be obtained the compound (pd) wherein the polyalkylene glycol chains at the 2- and 3-positions are non-reactive and only the polyalkylene glycol chain at the 1-position has a hydroxyl group among the three polyalkylene glycol chains. Furthermore, according to the bio-related substance to be modified, the moles of the alkylene oxide added can be controlled to adjust the chain length.

Moreover, by activating the hydroxyl group of the compound (p) and reacting a heterogeneous polyalkylene glycol derivative such as (pi), also the polyalkylene glycol derivative wherein only the polyalkylene glycol chain at the 1-position has a hydroxyl group can be selectively obtained. Also, the number of n can be adjusted according to the bio-related substance to be modified.

The following will describe a process for synthesizing the polyalkylene glycol derivative wherein X is a hydroxyl group in more detail.

The benzyl etherification of 2,2-dimethyl-1,3-dioxolane-4-methanol can be carried out in the following manner.

1) It can be achieved by reacting benzyl chloride or benzyl bromide with 2,2-dimethyl-1,3-dioxolane-4-methanol in an aprotic solvent or without any solvent in the presence of an alkali catalyst such as sodium hydroxide or potassium hydroxide.

2) It can be achieved by converting the hydroxyl group of 2,2-dimethyl-1,3-dioxolane-4-methanol in an aprotic solvent or without any solvent using sodium, potassium, sodium hydride, potassium hydride, sodium methoxide, potassium methoxide, potassium t-butoxide, or the like into an alcoholate and reacting the alcoholate with benzyl chloride or benzyl bromide under a basic condition.

3) It can be achieved by activating the hydroxyl group of 2,2-dimethyl-1,3-dioxolane-4-methanol with methanesulfonyl chloride, p-toluenesulfonyl chloride, 2,2,2-trifluoroethanesulfonyl chloride, or the like in an aprotic solvent or without any solvent, followed by the reaction with an alcoholate of benzyl alcohol.

The deprotection of the cyclic acetal structure which follows the benzyl etherification is achieved by the reaction in an aqueous solution adjusted to pH 1 to 4 with an acid such as acetic acid, phosphoric acid, sulfuric acid, or hydrochloric acid, whereby a compound of the formula (pa) can be produced.

The method of addition polymerization of an alkylene oxide to the compound of the formula (pa) having two hydroxyl groups newly formed by the deprotection of the cyclic acetal to obtain a compound of the formula (pb) is not particularly limited but can be achieved via the following steps (C1) and (C2).

Step (C1): as a method of alcoholation of the compound of the formula (pa), the alcoholation is carried out using sodium or potassium, preferably sodium as a catalyst, in an catalyst amount of 5 to 50% by mol, followed by dissolution at 10 to 50° C.

Step (C2): an alkylene oxide addition polymerization is carried out at a reaction temperature of 50 to 130° C.

With regard to the catalyst amount in the step (C1), since the polymerization rate of the alkylene oxide decreases at less than 5% by mol and heat history increases to result in the formation of impurities such as a terminal vinyl ether compound, the use of the catalyst in an amount of 5% by mol or more is advantageous in the production of a high quality high-molecular-weight compound. When the catalyst amount exceeds 50% by mol, the viscosity of the reaction liquid increases or the liquid solidifies at the alcoholation reaction and thus there is a tendency that the stirring efficiency decreases and the alcoholation is not accelerated. Moreover, when the liquid solidifies, handling thereof tends to be difficult, which causes water absorption. When the alcoholate has absorbed water, an alkylene glycol compound derived from water is formed and is contained as an impurity undesirable in medical use.

When the temperature at the dissolution is higher than 50° C., a decomposition reaction may occur to form benzyl alcohol and glycerin. When benzyl alcohol is formed, it initiates addition polymerization with the alkylene oxide, whereby a low-molecular-weight impurity having a molecular weight 0.5 time the molecular weight of the target compound. When the low-molecular-weight impurity derived from benzyl alcohol is formed, a functional group is introduced via alkyl-etherification of the hydroxyl group and deprotection in the subsequent steps as in the case of the target compound, so that the impurity is converted into a low-molecular-weight impurity which is reactive with a bio-related substance. There is a possibility that such impurity may react with a bio-related substance and change the physical properties of the resulting preparation. Moreover, when glycerin is formed, it also initiates addition polymerization with the alkylene oxide to form a high-molecular-weight impurity having a molecular weight 1.5 times that of the target compound. Since the high-molecular-weight impurity does not have a benzyl group and its terminal hydroxyl group is only alkyl-etherified, no functional group is introduced. However, when the combination with a drug or the like is carried out while such impurity is contained, the resulting preparation becomes inhomogeneous and hence the quality tends to be varied. Also, the preparation is not suitable in a medical use where a highly pure product is required.

When the dissolution is carried out at a temperature lower than 10° C., like the case that the catalyst amount is more than 50% by mol, the viscosity of the reaction liquid increases or the liquid solidified at the alcoholation reaction, and handling thereof tends to be difficult, and water absorption is caused.

The reaction solvent is not particularly limited as far as it is an aprotic solvent such as toluene, benzene, xylene, acetonitrile, ethyl acetate, tetrahydrofuran, chloroform, methylene dichloride, dimethyl sulfoxide, dimethylformamide, or dimethylacetamide, but preferable is toluene or no solvent. The reaction time is preferably 1 to 24 hours. When the time is shorter than 1 hour, there is a possibility that the catalyst does not completely dissolved. When the time is longer than 24 hours, there is a possibility that the above decomposition reaction may occur.

With regard to the reaction temperature in the step (C2), when the temperature is lower than 50° C., the polymerization rate is low and heat history increases to result in a tendency to decrease the quality of the compound of the formula (pb). Moreover, when the temperature is higher than 130° C., side reactions such as vinyl etherification of the terminal end occur during the polymerization and thus the quality of the target compound tends to decrease. During the polymerization, as the molecular weight increases, the viscosity of the reaction liquid also increases, so that an aprotic solvent, preferably toluene may be optionally added.

As another production process in the step of alcoholation, the following step (C3) may be mentioned.

Step (C3): Sodium methoxide, potassium t-butoxide, or potassium methoxide, preferably sodium methoxide is added as an catalyst in an amount of 5 to 80% by mol and the reaction is carried out at 60 to 80° C. At that time, a pressure-reducing operation may be conducted in order to facilitate the exchange reaction.

The catalyst amount is preferably 5 to 80% by mol for the reason mentioned above. With regard to the reaction temperature, when the temperature is lower than 60° C., the conversion of the exchange reaction decreases and alcohols such as methanol remain, which leads to the formation of impurities having a molecular weight 0.5 time that of the target compound via addition polymerization of an alkylene oxide. When the temperature is higher than 80° C., a decomposition reaction occurs. The alcoholation reaction requires elevation of the temperature and the reaction time is desirably 1 to 3 hours since the decomposition reaction is apt to occur. When the time is shorter than 1 hour, there is a possibility that the conversion into the alcoholate decreases. Where the time is longer than 3 hours, a decomposition reaction may occur. The reaction solvent is not particularly limited as far as it is an aprotic solvent, but preferable is toluene or no solvent.

The subsequent alkyl-etherification of the terminal end may be achieved by either of the following (1) or (2):

(1) a process of converting the terminal end of the polyalkylene glycol chain into an alcoholate and reacting it with an alkyl halide;

(2) a process of activating the terminal hydroxyl group of the polyalkylene glycol chain with methanesulfonyl chloride, p-toluenesulfonyl chloride, 2,2,2-trifluoroethanesulfonyl chloride, or the like, followed by the reaction with an alcoholate of an alkyl alcohol.

Preferable is the process (2) and the following will describe it in more detail.

The production process (2) comprises the following steps (B1), (B2), and (B3).

Step (B1): a step of adding a dehalogenating agent and a compound represented by the formula (6) to a compound represented by the formula (pb) and reacting them at 20 to 60° C. to obtain a compound of the formula (7). At that time, each charged molar ratio satisfies the following relationship:

$$Vc \geq 2\,Va$$

$$Vb > Vc$$

Va: number of moles of the compound represented by the formula (pb)

Vb: number of moles of the dehalogenating agent

Vc: number of moles of the compound represented by the formula (6).

More preferable is the case that the molar ratio satisfies the following relationship:

$$20\,Va \geq Vc \geq 2\,Va$$

$$4\,Vc > Vb > Vc.$$

When Vc is smaller than 2 Va, the conversion decreases and thus some of the hydroxyl groups in the oxyalkylene chain terminal ends remain unchanged. Thereafter, a functional group is introduced to the remaining hydroxyl group to form a polyfunctional impurity having a molecular weight the same as that of the target compound. When such a polyfunctional impurity is present, it acts as a crosslinking agent at the combination with a bio-related substance to result in a tendency to decrease the purity of the resulting modified bio-related substance. When Vb is not larger than Vc, the conversion decreases owing to inefficient trapping of an acid which is produced as a by-product with the progress of the reaction, so that some of the hydroxyl groups in the oxyalkylene chain terminal ends remain unchanged. Moreover, when Vc is larger than 20 Va or Vb is not smaller than 4 Vc, an excess amount may be contained to cause side reactions.

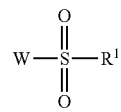

(6)

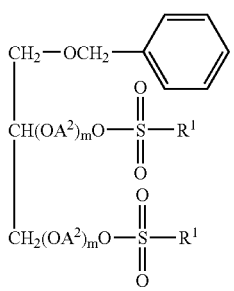

(7)

The dehalogenating agent to be used includes organic bases such as triethylamine, pyridine, and 4-dimethylaminopyridine, and inorganic bases such as sodium carbonate, sodium hydroxide, sodium hydrogen carbonate, sodium acetate, potassium carbonate, and potassium hydroxide. Preferable dehydrochlorinating agent is an organic base such as triethylamine, pyridine, or 4-dimethylaminopyridine.

In the compound of the formula (6) to be used, W is preferably Cl or Br, and $R^1$ is preferably a methyl group, a phenyl group, or a p-methylphenyl group. More suitably, methanesulfonyl chloride where W is Cl and $R^1$ is a methyl group is most preferable.

The solvent to be used at that time is not particularly limited as far as it is an aprotic solvent and preferably includes toluene, benzene, xylene, acetonitrile, ethyl acetate, tetrahydrofuran, chloroform, methylene dichloride, dimethyl sulfoxide, dimethylformamide, or dimethylacetamide, but more preferable is toluene which enables azeotropic removal of water in the system. The amount of the solvent to be used at the reaction is preferably 0.5 equivalent weight to 10 equivalent weight to the compound of the formula (pb). In the case that the compound of the formula (pb) has a large molecular weight, the viscosity of the reaction liquid increases and the conversion decreases, so that it is preferable to dilute the reaction liquid with the solvent.

The reaction temperature is not particularly limited but is preferably 60° C. or lower for the purpose of inhibiting side reactions and is preferably 20° C. or higher for the purpose of inhibiting increase of the viscosity of the reaction liquid. The reaction time is preferably 1 to 24 hours. When the time is shorter than 1 hour, there is a possibility that the conversion is low. When the time is longer than 24 hours, there is a possibility that a side reaction may occur.

At the reaction, the operation of removing water from the starting materials, such as azeotropic removal of water may be carried out prior to the reaction. Moreover, an antioxidant such as 2,6-di-tert-butyl-p-cresol (BHT) may be added. Furthermore, a salt is formed with the progress of the reaction and the formation of the compound of the formula (7), but the reaction mixture may be used in the subsequent step as it is, or the salt may be removed by filtration, or after the filtration, the compound of the formula (7) may be purified by a purification means such as extraction, recrystallization, adsorption treatment, reprecipitation, column chromatography, or supercritical extraction.

Step (B2): a step of adding a compound represented by the formula (8) to the compound of the formula (7) and reacting them at 20 to 80° C to obtain the compound of the formula (pc). At that time, each charged molar ratio satisfies the following relationship:

$$Vd>Vc$$

Vd: number of moles of the compound represented by the formula (8).

More preferable is the case that the relationship:

$$10Vc>Vd>Vc$$

is satisfied.

$$R—OM \qquad (8)$$

In the formula (8), R is as mentioned above and M is sodium or potassium, preferably sodium.

When Vd is not larger than Vc, the alkyl-etherification does not sufficiently proceed and a reactive group such as a mesylate group remains unchanged at the oxyalkylene chain terminal end. When a reactive group remains at the oxyalkylene chain terminal end, as mentioned above, a polyfunctional compound is formed and a serious side reaction is caused at the combination with a bio-related substance. Moreover, when Vd is not smaller than 10Vc, an excess of the alcoholate may be contained to cause side reactions in the subsequent process.

The solvent to be used in the reaction is not particularly limited as far as it is an aprotic solvent as mentioned above and is preferably toluene. The amount of the solvent to be used at the reaction is preferably an amount of 0.5 equivalent by weight to 10 equivalents by weight to the compound of the formula (7). In the case that the compound of the formula (7) has a large molecular weight, the viscosity of the reaction liquid increases, so that it is preferable to dilute the reaction liquid with the solvent.

The reaction temperature is not particularly limited but is preferably 80° C. or lower for the purpose of inhibiting side reactions and is preferably 20° C. or higher for the purpose of inhibiting increase of the viscosity of the reaction liquid. The reaction time is preferably 1 to 24 hours. When the time is shorter than 1 hour, there is a possibility that the conversion is low. When the time is longer than 24 hours, there is a possibility that a side reaction occurs. At the reaction, an operation of removing water from the starting materials, such as azeotropic removal of water may be carried out prior to the reaction.

Step (B3): a step of filtrating the reaction liquid or washing the reaction liquid with an aqueous inorganic salt solution having a concentration of 10% by weight or more.

In the step, the inorganic salt is not particularly limited but is preferably sodium chloride. When the concentration is less than 10% by weight, the target compound migrates into an aqueous layer to decrease the process yield remarkably. The operation of washing with water may be repeated several times. The step (133) is carried out for removing starting materials excessively added and salts produced as by-products. The omission of the step may cause side reactions in the case that the steps (B11) to (B3) are again carried out in the next place. In the case that a debenzylation step is carried out as a next step, these impurities act as catalyst poisons and thus the conversion may be affected.

Moreover, in order to enhance the ratio of alkyl-etherification of the oxyalkylene chain terminal end, it is preferable to repeat the steps (B1) to (B3) again. When the ratio of alkyl-etherification of the oxyalkylene chain terminal end is low, as mentioned above, there is a possibility of forming a polyfunctional impurity.

The compound of the formula (pc) thus obtained may be purified by a purification means such as extraction, recrystallization, adsorption treatment, reprecipitation, column chromatography, or supercritical extraction.

The production of the compound (p) by successive debenzylation is not particularly limited but it can be produced by hydrogenation of the following step (A) using a hydrogenative reduction catalyst and a hydrogen donor.

Step (A): a step of subjecting the compound represented by the formula (pc) to a hydrogenative reduction reaction under the condition that the water content in the reaction system is 1% or less. When the water content in the reaction system is more than 1%, the decomposition reaction of the polyoxyalkylene chain occurs. Since polyalkylene glycol formed by the decomposition has a hydroxyl group, it is functionalized in the next step to form a reactive low-molecular-weight impurity. Such a reactive low-molecular-weight impurity reacts with a bio-related substance as mentioned above and thus tends to change the properties of the resulting preparation.

The hydrogenative reduction catalyst is preferably palladium. The support is not particularly limited but is preferably alumina or carbon, more preferably carbon. The amount of palladium is preferably 1 to 20% by weight based on the compound of the formula (4). When the amount is less than 1% by weight, the conversion of deprotection decreases and thus there is a possibility that the ratio of functionalization in the next step decreases. Moreover, when the amount is more than 20% by weight, the decomposition reaction of the polyalkylene glycol chain may occur and there is a possibility that the above reactive low-molecular-weight compound is produced as a by-product. The reaction solvent is not particularly limited as far as the water content in the reaction system is less than 1%, but preferably includes methanol, ethanol, 2-propanol, and the like and more preferable is methanol. The hydrogen donor is not particularly limited but include hydrogen gas, cyclohexene, 2-propanol, and the like. The reaction temperature is preferably 40° C. or lower. When the temperature is higher than 40° C., the decomposition reaction of the polyalkylene glycol chain may occur and there is a possibility that the reactive low-molecular-weight compound is produced as a by-product. The reaction time is not particularly limited. When large amount of the catalyst is used, the reaction is completed within a short period of time. But, when the amount is small, a longer period of time is required. In general, the reaction time is preferably 1 to 5 hours. When the time is shorter than 1 hour, there is a possibility that the conversion is low. When it is longer than 5 hours, the decomposition reaction of the poly(alkylene glycol) may occur.

The resulting compound of the formula (p) may be purified by a purification means such as extraction, recrystallization, adsorption treatment, reprecipitation, column chromatography, or supercritical extraction.

The thus obtained compound is a polyalkylene glycol derivative represented by the following formula (p):

(p)

wherein R is a hydrocarbon group having 1 to 24 carbon atoms, $OA^2$ is an oxyalkylene group having 2 to 4 carbon atoms, the groups represented by R are the same or different from each other in one molecule, the groups represented by $OA^2$ are the same or different from each other in one molecule, m is an average number of moles of the above oxyalkylene group added, and m represents 10 to 1000.

The compound of the formula (p) is a compound having non-reactive polyalkylene glycol chains at the 2- and 3-positions of glycerin and having a primary hydroxyl group at the 1-position. Since the compound of the formula (p) contains substantially no secondary hydroxyl group, conversion of the subsequent reaction of introducing a polyalkylene glycol chain is high and a highly pure polyalkylene glycol derivative can be obtained. In the case that a secondary hydroxyl group is present, the conversion of the reaction of introducing a polyalkylene glycol chain is low and decrease in purity is induced.

The compound (p) thus obtained has a low content of the impurities having a hydroxyl group at the terminal end of the polyoxyalkylene chain shown below.

(A): an impurity having a hydroxyl group and a molecular weight 0.5 time that of the compound (p), which is formed by decomposition of the compound of the formula (pa) at the alcoholation, addition polymerization of an alkylene oxide to the resulting benzyl alcohol, and deprotection of benzyl group in the subsequent step;

(B): an impurity having a remaining hydroxyl group at 2- or 3-position and a molecular weight the same as that of the compound (p), which is formed at the alkyl-etherification of the compound of the formula (pb);

(C): an impurity having a hydroxyl group and a low molecular weight, which is formed by decomposition of the polyoxyalkylene chain at the debenzylation of the compound of the formula (pc).

When introduction of a polyalkylene glycol chain and subsequent introduction of a functional group are carried out using a compound (p) containing a large amount of impurities (A), (B), and (C), impurities of the reactive polyalkylene glycol derivatives shown below are contained.

(D): a low-molecular-weight reactive polyalkylene glycol derivative, wherein a polyalkylene glycol chain and a functional group are introduced into the impurity shown in the above (A);

(E): a bifunctional or trifunctional reactive polyalkylene glycol derivative, wherein a polyalkylene glycol chain and a functional group are introduced into the impurity shown in the above (B);

(F): a low-molecular-weight reactive polyalkylene glycol derivative, wherein a polyalkylene glycol chain and a functional group are introduced into the impurity shown in the above (C).

Subsequently, there will be described a process for synthesizing a compound wherein X is a hydroxyl group in the formula (1) from the compound (p) by introducing a polyalkylene glycol chain to the 1-position of the glycerin skeleton.

(Case of Carrying out Oxyalkylene Addition Polymerization)

The method of addition polymerization of an alkylene oxide to the compound of the formula (p) to obtain a compound of the formula (pd) is not particularly limited but can be achieved via the aforementioned steps (C3) and (C2).

Step (C3): Sodium methoxide, potassium t-butoxide, or potassium methoxide, preferably sodium methoxide is added as an catalyst in an amount of 5 to 80% by mol and the reaction is carried out at 60 to 80° C. At that time, a pressure-reducing operation may be conducted in order to facilitate the exchange reaction.

Step (C2): an alkylene oxide addition polymerization is carried out at a reaction temperature of 50 to 130° C.

For the reason as mentioned above, the catalyst amount is preferably 5 to 80% by mol to the compound (p). With regard to the reaction temperature, when the temperature is lower than 60° C., conversion of the exchange reaction decreases and an alcohol such as methanol remains, so that a low-molecular-weight linear polyalkylene glycol is formed via addition polymerization of the alkylene oxide. When the temperature is higher than 80° C., decomposition reaction occurs. In the alcoholation reaction, it is necessary to elevate the temperature and the reaction time is desirably 1 to 3 hours because the decomposition reaction is apt to occur. When the time is shorter than 1 hour, there is a possibility that conversion of the alcoholation may decrease. When the time is longer than 3 hours, there is a possibility that the decomposition reaction may occur. The reaction solvent is not particularly limited as far as it is an aprotic solvent but preferable is toluene or no solvent.

As mentioned above, with regard to the reaction temperature in the step (C2), when the temperature is lower than 50° C., the polymerization rate is low and heat history increases to result in a tendency to decrease the quality of the compound of the formula (pd). Moreover, when the temperature is higher than 130° C., side reactions such as vinyl etherification of the terminal end occur during the polymerization and thus the quality of the target compound tends to decrease. During the polymerization, as the molecular weight increases, the viscosity of the reaction liquid also increases, so that an aprotic solvent, preferably toluene may be optionally added.

(Case of Using Heterogeneous Polyalkylene Glycol)

In the case of using a heterogeneous polyalkylene glycol, the hydroxyl group of the compound (p) is activated, for example, compound of the formula (pe), (pf), (pg), or (ph) is synthesized, followed by reaction with a heterogeneous polyalkylene glycol. The process for synthesizing the compound of the formula (pe), (pf), (pg), or (ph) by modifying the compound (p) is the same as the process for synthesizing X to be mentioned below.

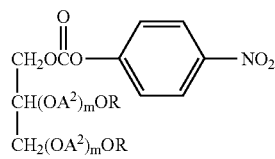
(pe)

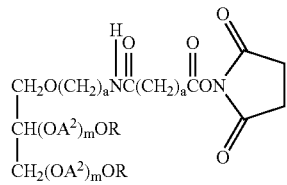
(pf)

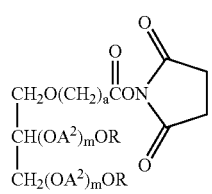
(pg)

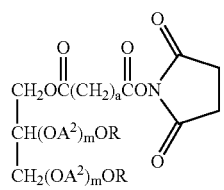
(ph)

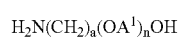
(pi)

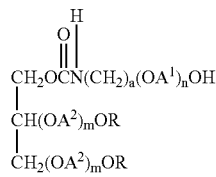
(pe1)

In the formulae (pe), (pf), (pg), and (ph), R, $OA^2$, $OA^1$, m, and n are the same as mentioned above. a represents an integer of 1 to 6 and may be the same or different from each other. More preferably, a is an integer of 2 to 5.

The heterogeneous polyalkylene glycol is not particularly limited but preferably, the compound of the formula (pi) is used.

$$H_2N(CH_2)_a(OA^1)_nOH \quad (pi)$$

In the formula (pi), $OA^1$, n, and a are as mentioned above.

The reaction of the formula (pe) with (pi) is carried out in an aprotic solvent such as toluene, benzene, xylene, acetonitrile, ethyl acetate, diethyl ether, t-butyl methyl ether, tetrahydrofuran, chloroform, methylene dichloride, dimethyl sulfoxide, dimethylformamide, or dimethylacetamide or without any solvent. The heterogeneous polyalkylene glycol of (pi) is used in an amount of preferably equimolar or more, more preferably equimolar to 5 mol to the compound (pe). A catalyst, e.g., an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide may be added. The ratio of the organic base or inorganic base to be used is not particularly limited but is preferably equimolar or more to the compound (pi). Moreover, an organic base may be used as a solvent. The reaction temperature is preferably 0 to 200° C., more preferably 20 to 100° C. The reaction time is preferably 10 minutes to 48 hours, more preferably 30 minutes to 12 hours. During the reaction, light shielding may be conducted. The compound formed may be purified by a purification means such as extraction, recrystallization, adsorption treatment, reprecipitation, ion-exchange chromatography, supercritical extraction, ion-exchange resin, or gel permeation chromatography.

The reaction of (pf), (pg), or (ph) with (pi) is carried out in an aprotic solvent mentioned above or without any solvent. The heterogeneous polyalkylene glycol of (pi) is used in an amount of preferably equimolar or more, more preferably equimolar to 5 mol to the compound (pe), (pg), or (ph). A catalyst, e.g., an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide may be added. The ratio of the organic base or inorganic base to be used is not particularly limited but is preferably equimolar or more to the compound (pi). Moreover, an organic base may be used as a solvent. The reaction temperature is preferably 0 to 200° C., more preferably 20 to 60° C. The reaction time is preferably 10 minutes to 48 hours, more preferably 30 minutes to 12 hours. During the reaction, light shielding may be conducted. The compound formed may be purified by the aforementioned purification means.

Using the hydroxyl group of the compound (pd), (pe1), (pf1), (pg1), or (ph1), the polyalkylene glycol derivatives of the invention can be produced by conversion into various reactive groups shown in group(I).

Subsequently, synthetic processes from a hydroxyl group to various reactive groups shown in the group (I) will be described but the other known processes may be used for the synthesis. The following will describe a case that the compound (pd) is used as an example.

(Process for Producing (a))

The amine compound (a) can be obtained by adding the compound (pd) to acrylonitrile or the like using an inorganic base such as sodium hydroxide or potassium hydroxide in a solvent such as water or acetonitrile to obtain a nitrile compound and then subjecting it to hydrogenation of the nitrile group in the presence of a nickel or palladium catalyst in an autoclave. The ratio of the inorganic base to be used for obtaining the nitrile compound is not particularly limited but is preferably 0.01 to 50% by weight to the compound (pd). The ratio of acrylonitrile or the like to be used is not particularly limited but is preferably 0.5 to 5 equivalent weight, more preferably 1 to 4 equivalent weight to the weight of the compound (pd). Moreover, acrylonitrile may be used as a solvent. The reaction temperature is preferably −50 to 100° C., more preferably −20 to 60° C. The reaction time is preferably 10 minutes to 48 hours, more preferably 30 minutes to 24 hours. The reaction solvent in the subsequent hydrogenation reaction of the nitrile compound is not particularly limited as far as it does not participate in the reaction, but is preferably toluene. The ratio of the nickel or palladium catalyst to be used is not particularly limited but is 0.05 to 30% by weight, preferably 0.5 to 20% by weight to the nitrile compound. The reaction temperature is preferably 20 to 200° C., more preferably 50 to 150° C. The reaction time is preferably 10 minutes to 48 hours, more preferably 30 minutes to 24 hours. The hydrogen pressure is preferably 2 to 10 MPa, more preferably 3 to 8 MPa. Moreover, in order to prevent dimerization, ammonia may be added to the reaction system. In the case of adding ammonia, ammonia pressure is not particularly limited but is 0.1 to 10 MPa, more preferably 0.3 to 2 MPa. The compound formed may be purified by a purification means such as extraction, recrystallization, adsorption treatment, reprecipitation, ion-exchange chromatography, supercritical extraction, ion-exchange resin, or gel permeation chromatography.

(Process for Producing (d))

By reacting the compound (pd) with an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide and any one of the compounds represented by the following general formula (d1) in an aprotic solvent such as toluene, benzene, xylene, acetonitrile, ethyl acetate, diethyl ether, t-butyl methyl ether, tetrahydrofuran, chloroform, methylene dichloride, dimethyl sulfoxide, dimethylformamide, or dimethylacetamide or without any solvent, the compound (d) can be synthesized. Moreover, the above organic base or inorganic base need not be used. The ratio of the organic base or inorganic base to be used is not particularly limited but is preferably equimolar or more to the compound (pd). Furthermore, an organic base may be used as a solvent. W in (d1) is a halogen atom selected from Cl, Br and I, and is preferably Cl. The ratio of the compound represented by the general formula (d1) to be used is not particularly limited but is preferably equimolar or more, more preferably equimolar to 50 molar to the compound (pd). The reaction temperature is preferably 0 to 300° C., more preferably 20 to 150° C. The reaction time is preferably 10 minutes to 48 hours, more preferably 30 minutes to 24 hours. The compound formed may be purified by a purification means such as extraction, recrystallization, adsorption treatment, reprecipitation, ion-exchange chromatography, supercritical extraction, ion-exchange resin, or gel permeation chromatography.

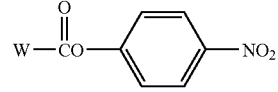

(d1)

wherein W is a halogen atom selected from Cl, Br, and I.

(Process for Producing (c) and (h))

The succinimide compound (c) can be obtained by reacting the compound (pd) with a dicarboxylic acid anhydride such as succinic anhydride or glutaric anhydride to obtain a carboxyl compound (h), followed by condensation with N-hydroxysuccinimide in the presence of a condensing agent such as DCC or EDC. The reaction of the compound (pd) with a dicarboxylic acid anhydride is carried out in the aforementioned aprotic solvent or without any solvent. The ratio of the dicarboxylic acid anhydride to be used is not particularly limited but is preferably equimolar or more, more preferably equimolar to 5 molar to the compound (pd). The reaction temperature is preferably 0 to 200° C., more preferably 20 to 150° C. The reaction time is preferably 10 minutes to 48 hours, more preferably 30 minutes to 12 hours. In the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 50% by weight, more preferably 0.5 to 20% by weight. The carboxyl compound (h) thus formed may be purified by the aforementioned purification means or may be used as it is in the next condensation reaction.

The subsequent condensation reaction is also carried out in the aforementioned aprotic solvent or without any solvent. The condensing agent is not particularly limited but is preferably DCC. The ratio of DCC to be used is preferably equimolar or more, more preferably equimolar to 5 molar to the compound (h). The ratio of N-hydroxysuccinimide to be used is preferably equimolar or more, more preferably equimolar to 5 molar to the compound (h). The reaction temperature is preferably 0 to 100° C., more preferably 20 to 80° C. The reaction time is preferably 10 minutes to 48 hours, more preferably 30 minutes to 12 hours. The compound formed may be purified by the aforementioned purification means.

Moreover, the compound (c) can be, for example, produced by the following process. It can be obtained by reacting the compound (pd) with N,N'-disuccinimidyl carbonate. The reaction of the compound (pd) with N,N'-disuccinimidyl carbonate is carried out in the aforementioned aprotic solvent or without any solvent. The ratio of N,N'-disuccinimidyl carbonate to be used is not particularly limited but is preferably equimolar or more, more preferably equimolar to 20 molar to the compound (pd). The reaction temperature is preferably 0 to 200° C., more preferably 20 to 150° C. The reaction time is preferably 10 minutes to 48 hours, more preferably 30 minutes to 12 hours. In the reaction, an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide may be used as a catalyst. The ratio of the catalyst to be used is preferably 0.1 to 50% by weight, more preferably 0. 5 to 20% by weight. The compound (c) thus formed may be purified by the aforementioned purification means.

(Process for Producing (b))

Furthermore, the maleimide compound (b) can be obtained by reacting the resulting amine (a) with maleic anhydride in the aforementioned aprotic solvent or without any solvent to obtain an maleamide compound and then subjecting it to a ring closure reaction using acetic anhydride or sodium acetate as a catalyst. The ratio of maleic anhydride to be used in the maleamidation reaction is not particularly limited but is preferably equimolar or more, more preferably equimolar to 5 molar to the compound (pd). The reaction temperature is preferably 0 to 200° C., more preferably 20 to 120° C. The reaction time is preferably 10 minutes to 48 hours, more preferably 30 minutes to 12 hours. The maleamide compound formed may be purified by the aforementioned purification means or may be used as it is in the next ring closure reaction.

The reaction solvent in the subsequent ring closure reaction is not particularly limited but is preferably aprotic solvent or acetic anhydride. The ratio of sodium acetate to be used is not particularly limited but is preferably equimolar or more, more preferably equimolar to 50 molar to the maleamide compound. The reaction temperature is preferably 0 to 200° C., more preferably 20 to 150° C. The reaction time is preferably 10 minutes to 48 hours, more preferably 30 minutes to 12 hours. The compound formed may be purified by the aforementioned purification means.

The maleimide compound (b) can be also obtained by reacting the compound of the following formula (bI) with the aforementioned amine (a). The reaction is carried out in the aforementioned aprotic solvent or without any solvent and the compound (b 1) is added in an amount of equimolar or more to the amine (a), followed by reaction. The ratio of (b 1) to be used is preferably equimolar or more, more preferably equimolar to 5 molar to (a). The reaction temperature is preferably 0 to 200° C., more preferably 20 to 80° C. The reaction time is preferably 10 minutes to 48 hours, more preferably 30 minutes to 12 hours. During the reaction, light shielding may be conducted. The compound formed may be purified by the aforementioned purification means.

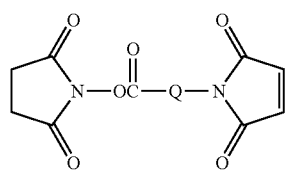
(b1)

wherein Q represents a hydrocarbon group having 1 to 7 carbon atoms.

(Process for Producing (i))

The mercapto compound (i) can be obtained by reacting the compound (pd) with methanesulfonyl chloride in the presence of a base to effect mesylation, followed by the reaction with a thiol-forming agent such as thiourea. The reaction solvent in the mesylation reaction is preferably the above aprotic solvent or without any solvent. The base is preferably an organic base such as triethylamine, pyridine, or 4-dimethylaminopyridine or an inorganic base such as sodium carbonate, sodium hydroxide, sodium hydrogen carbonate, sodium acetate, potassium carbonate, or potassium hydroxide. The ratio of the organic base or inorganic base to be used is not particularly limited but is preferably equimolar or more to the compound (pd). Also, the organic base may be used as a solvent. The ratio of methanesulfonyl chloride to be used is not particularly limited but is preferably equimolar or more, more preferably equimolar to 50 molar to the compound (pd). The reaction temperature is preferably 0 to 300° C., more preferably 20 to 150° C. The reaction time is preferably 10 minutes to 48 hours, more preferably 30 minutes to 24 hours. The compound formed may be purified by a purification means such as extraction, recrystallization, adsorption treatment, reprecipitation, ion-exchange chromatography, supercritical extraction, ion-exchange resin, or gel permeation chromatography.

The thiol-formation reaction is carried out in a solvent such as water, an alcohol, or acetonitrile or without any solvent. The ratio of thiourea to be used is equimolar or more, more preferably equimolar to 50 molar to the mesylated compound. The reaction temperature is preferably 0 to 300° C., more preferably 20 to 150° C. The reaction time is preferably 10 minutes to 48 hours, more preferably 30 minutes to 24 hours. After completion of the reaction, the mercapto compound can be obtained by subjecting the resulting thiazolium salt to alkali hydrolysis. The compound formed may be purified by the aforementioned purification means.

Moreover, the above mercapto compound can be also obtained by reacting the mesylated compound with the following compound (i1), followed by decomposition with a primary amine. The reaction of the mesylated compound with the compound (i1) is carried out in the aforementioned aprotic solvent or without any solvent. The ratio of the compound (i1) to be used is equimolar or more, more preferably equimolar to 50 molar to the compound (pd). The reaction temperature is preferably 0 to 300° C., more preferably 20 to 80° C. The reaction time is preferably 10 minutes to 48 hours, more preferably 30 minutes to 24 hours. The subsequent alkali decomposition with a primary amine is carried out in the aforementioned aprotic solvent or without any solvent. The primary amine to be used is not particularly limited but preferably includes ammonia, methylamine, ethylamine, propylamine, butylamine, pentylamine, hexylamine, cyclohexylamine, ethanolamine, propanolamine, butanolamine, and thle like. Naturally, the primary amine may be used as a solvent. The compound formed may be purified by the aforementioned purification means.

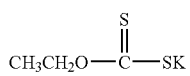
(i1)

(Process for Producing (e))

A haloacetyl compound (e) can be, for example, synthesized by the following process. It can be obtained by reacting the compound (pd) or the compound (a) with an organic base such as triethylamine, pyridine, or dimethylaminopyridine or an inorganic base such as sodium carbonate, sodium hydroxide, sodium hydrogen carbonate, sodium acetate, potassium carbonate, or potassium hydroxide and a compound represented by the following general formula (e1) in an aprotic solvent such as toluene, benzene, xylene, acetonitrile, ethyl acetate, diethyl ether, t-butyl methyl ether, tetrahydrofuran, chloroform, methylene dichloride, dimethyl sulfoxide, dimethylformamide, or dimethylacetamide, or without any solvent. The ratio of the organic base or inorganic base to be used is not particularly limited but is preferably equimolar or more to the compound (pd) or (a). Furthermore, an organic base may be used as a solvent. When the compound (a) is used, the above organic base or inorganic base may not be used. $W^1$ in (e1) is a halogen atom selected from Cl, Br, and I, and is preferably I. Moreover, the groups represented by $W^1$ may be the same or different from each other. The ratio of the compounds represented by the formula (e1) to be used is not particularly limited but is preferably equimolar or more, more preferably equimolar to 50 molar to the compound (pd) or (a). The reaction temperature is preferably 0 to 300° C., more preferably 20 to 150° C. The reaction time is preferably 10 minutes to 48 hours, more preferably 30 minutes to 24 hours. The compound formed may be purified by a purification means such as extraction, recrystallization, adsorption treatment, reprecipitation, ion-exchange chromatography, supercritical extraction, ion-exchange resin, or gel permeation chromatography.

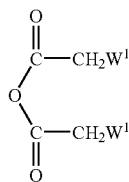

(e1)

(Process for Producing (f))

The compound (f) can be, for example, prepared by the following process. The hydrazine derivative (f) can be obtained by condensing the compound (h) with the following compound (f1) in the presence of a condensing agent such as DCC, EDC, or BOP [(benzotriazolyloxy) tris(dimethylamino)phosphonium hexafluorophosphate]. The reaction of the compound (h) with (f1) is carried out in the above aprotic solvent or without any solvent. The ratio of (f1) to be used is not particularly limited but is preferably equimolar or more, more preferably equimolar to 5 molar to the compound (h). The condensing agent is not particularly limited but is preferably DCC, EDC, or BOP. The ratio of the condensing agent to be used is not particularly limited but is preferably equimolar or more, more preferably equimolar to 5 molar to the compound (h). The reaction temperature is preferably 0 to 100° C., more preferably 20 to 80° C. The reaction time is preferably 10 minutes to 48 hours, more preferably 30 minutes to 12 hours. The compound formed may be purified by the aforementioned purification means.

NH$_2$NH-Boc    (f1)

wherein the Boc group means a t-butoxycarbonyl group.

Subsequent deprotection of the Boc group can be carried out by a known method. The compound (f) synthesized may be purified by the aforementioned purification means.

(Process for Producing (g))

The compound (g) can be, for example, prepared by the following process. The hydroxylamine derivative (g) can be obtained by condensing the compound (pd) or (a) with the following compound (g1) in the presence of a condensing agent such as DCC, EDC, or BOP [(benzotriazolyloxy) tris (dimethylarino)phosphonium hexafluorophosphate]. The reaction of the compound (pd) or (a) with (g1) is carried out in the above aprotic solvent or without any solvent. The ratio of (g1) to be used is not particularly limited but is preferably equimolar or more, more preferably equimolar to 5 molar to the compound (pd) or (a). The condensing agent is not particularly limited but is preferably DCC, EDC, or BOP. The ratio of the condensing agent to be used is not particularly limited but is preferably equimolar or more, more preferably equimolar to 5 molar to the compound (pd) or (a). The reaction temperature is preferably 0 to 100° C., more preferably 20 to 80° C. The reaction time is preferably 10 minutes to 48 hours, more preferably 30 minutes to 12 hours. The compound formed may be purified by the aforementioned purification means.

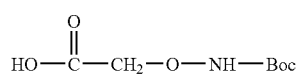

(g1)

Subsequent deprotection of the Boc group can be carried out by a known method. The compound (g) synthesized may be purified by the aforementioned purification means.

(Process for Producing (j))

The aldehyde compound (j) can be obtained by reacting the mesylated product of the compound (pd) with an acetal compound (j1) to obtain an acetal compound and then subjecting it to hydrolysis under an acidic condition. The production of the mesylated compound is as shown in the production process of (i). The acetalization reaction can be achieved by the reacting with an equimolar or more, preferably an equimolar to 50 molar of (j1) to the mesylated compound in the aforementioned aprotic solvent or without any solvent. (j1) can be prepared from the corresponding alcohol using sodium, potassium, sodium hydride, potassium hydride, sodium methoxide, potassium t-butoxide, or the like. The reaction temperature is preferably 0 to 300° C., more preferably 20 to 150° C. The reaction time is preferably 10 minutes to 48 hours, more preferably 30 minutes to 24 hours.

In the case of using (j2), an acetal compound can be obtained by converting the hydroxyl group of the compound (pd) into an alcoholate by the aforementioned process and then reacting it with an equimolar or more, preferably an equimolar to 100 molar of (j2) in the aforementioned aprotic solvent or without any solvent. The reaction temperature is preferably 0 to 300° C., more preferably 20 to 150° C. The reaction time is preferably 10 minutes to 48 hours, more preferably 30 minutes to 24 hours.

In the case of using (j3), an acetal compound can be obtained by reacting (j3) with (c), (d), or (h). The production of (c), (d), or (h) is as mentioned above. In the reaction with (j3), the solvent is not particularly limited but the reaction is preferably carried out in the aforementioned aprotic solvent. The charging ratio of (j3) is preferably equimolar or more, more preferably equimolar to 10 molar to (c), (d), or (h). The reaction temperature is preferably −30 to 200° C., more preferably 0 to 150° C. The reaction time is preferably 10 minutes to 48 hours, more preferably 30 minutes to 24 hours. In the case of using (h), a condensing agent such as DCC or EDC may be optionally used. Any acetalization reaction may be carried out under light shielding. The acetal compound thus obtained may be purified by the aforementioned purification means or may be used as it is in the next aldehyde-formation reaction.

The aldehyde compound can be produced by dissolving the acetal compound to form a 0.1 to 50% aqueous solution and hydrolyzing it in an aqueous solution which is adjusted to pH 1 to 4 with an acid such as acetic acid, phosphoric acid, sulfuric acid, or hydrochloric acid. The reaction temperature is preferably −20 to 100° C., more preferably 0 to 80° C. The reaction time is preferably 10 minutes to 24 hours, more preferably 30 minutes to 10 hours. The reaction may be carried out under light shielding. The compound formed may be purified by the aforementioned purification means.

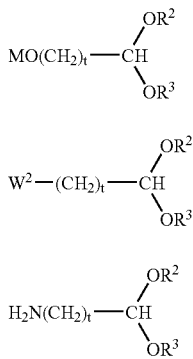

(j1)

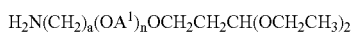

(j2)

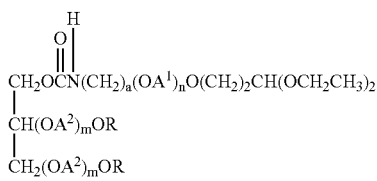

(j3)

wherein $R^2$ and $R^3$ are each a hydrocarbon group having 1 to 3 carbon atoms and may be the same or different from each other, and they may together form a ring; M is sodium or potassium; $W^2$ is a halogen atom selected from Cl, Br, and I; and t is an integer of 1 to 5.

The compound of the formula (1) of the invention can be synthesized from the compound having a terminal hydroxyl group, such as (pd), (pe1), (pf1), (pg1), or (ph1) as mentioned above, but can also be synthesized through one-step reaction using a heterogeneous polyalkylene glycol having a reactive group. For example, the hydroxyl group of the compound (p) is activated to synthesize the compound of the formula (pe), (pf), (pg), or (ph). With the compound, a heterogeneous polyalkylene glycol represented by the formula (pj) is reacted to obtain an acetal compound represented by the following formula (pe2), (pf2), (pg2), or (ph2). Furthermore, by hydrolyzing the compound under an acidic condition, there can be obtained an aldehyde compound represented by the following formula (pe3), (pB), (pg3), or (ph3), wherein X is (j).

$H_2N(CH_2)_a(OA^1)_nOCH_2CH_2CH(OCH_2CH_3)_2$ (pj)

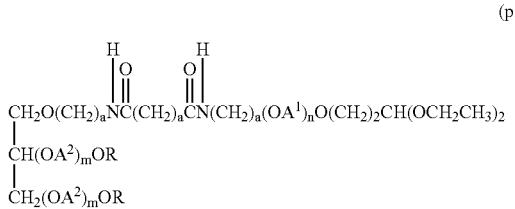

(pe2)

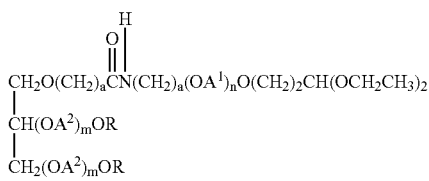

(pf2)

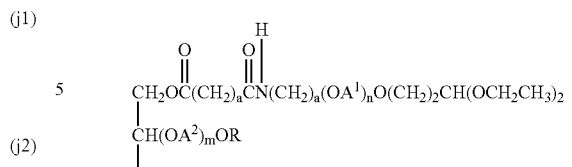

(pg2)

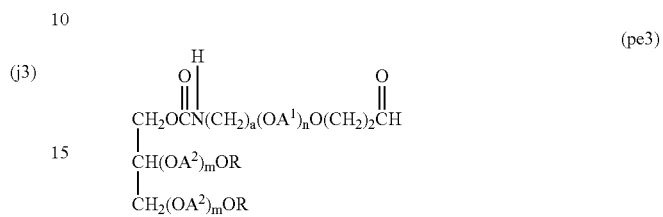

(ph2)

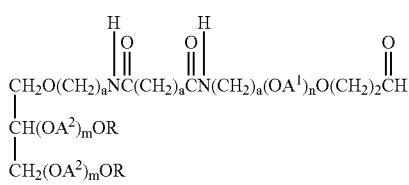

(pe3)

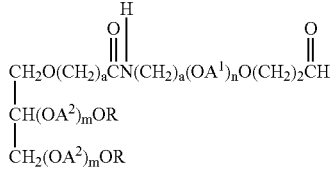

(pf3)

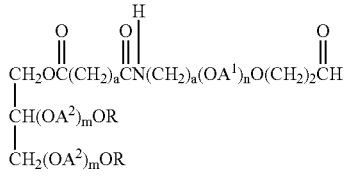

(pg3)

CH$_2$O(CH$_2$)$_a$CN(CH$_2$)$_a$(OA$^1$)$_n$O(CH$_2$)$_2$CH
|
CH(OA$^2$)$_m$OR
|
CH$_2$(OA$^2$)$_m$OR (ph3)

CH$_2$OC(CH$_2$)$_a$CN(CH$_2$)$_a$(OA$^1$)$_n$O(CH$_2$)$_2$CH
|
CH(OA$^2$)$_m$OR
|
CH$_2$(OA$^2$)$_m$OR

In the formulae (pj), (pe2), (pf), (pg2), (pCh2), (pe3), (pB), (pg3), and (ph3), R. $OA^2$, $OA^1$, m, n, and a are as mentioned above.

The conditions for the reaction of the compound (pe), (pf), (pg), or (ph) with the heterogeneous polyalkylene glycol derivative (pj) having an amino group are the same as those in the case of using (pi). Also, the reaction conditions for hydrolyzing the resulting acetal conipound to obtain the compound (pe3), (pf3), (pg3), or (ph3) are the same as those in the process for obtaining the above functional group (j).

Moreover, with the formula (pe), (pf), (pg), or (ph), a heterogeneous polyalkylene glycol represented by the formula (pk) can be reacted to obtain a carboxyl compound represented by the following formula (pe4), (pf4), (pg4), or (ph4), wherein X is (h). Furthermore, by reacting the compound with N-hydroxysuccinimide, there can be obtained a succinimide ester represented by the following formula (pe5), (pf5), (pg5), or (ph5), wherein X is (c).

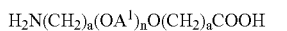(pk)

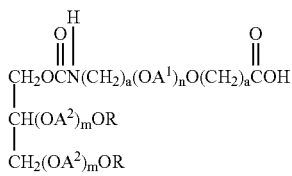(pe4)

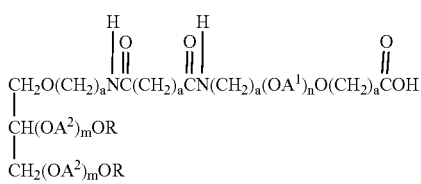(pf4)

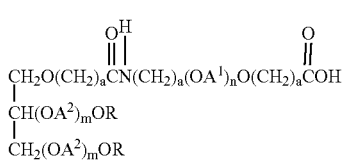(pg4)

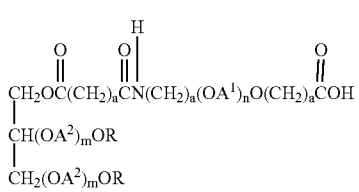(ph4)

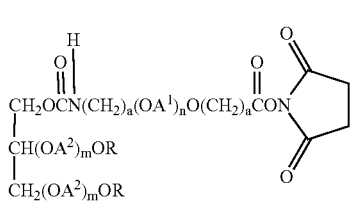(pe5)

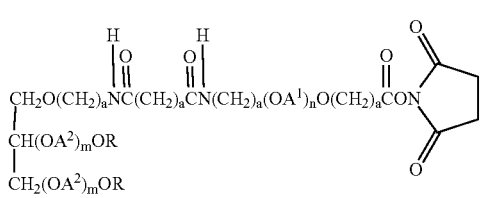(pf5)

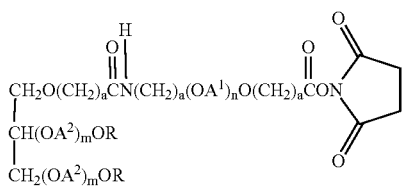(pg5)

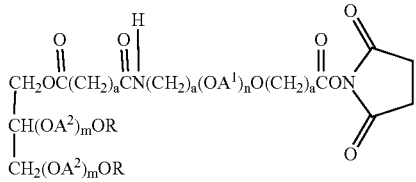(ph5)

In the formulae (pk), (pe4), (pf4), (pg4), (ph4), (pe5), (pf5), (pg5), and (ph5), R, $OA^2$, $OA^1$, m, n, and a are as mentioned above.

The conditions for the reaction of the compound (pe), (pf), (pg), or (ph) with the heterogeneous polyalkylene glycol derivative (pk) having an amino group are the same as those in the case of using (pi). Also, the reaction conditions for obtaining the compound (pe5), (pf5), (pg5), or (ph5) using the resulting carboxyl compound are the same as those in the process for obtaining the above functional group (c).

Furthermore, with the following formula (pm), a heterogeneous polyalkylene glycol represented by the formula (pl) or (pn) can be reacted to obtain a maleimide compound wherein X is (b) in the following formula (pm1) or (pm2). An amine compound wherein X is (a) in (pm4) can be obtained by reacting the following formula (po) with the formula (pm) and deprotecting the Boc group.

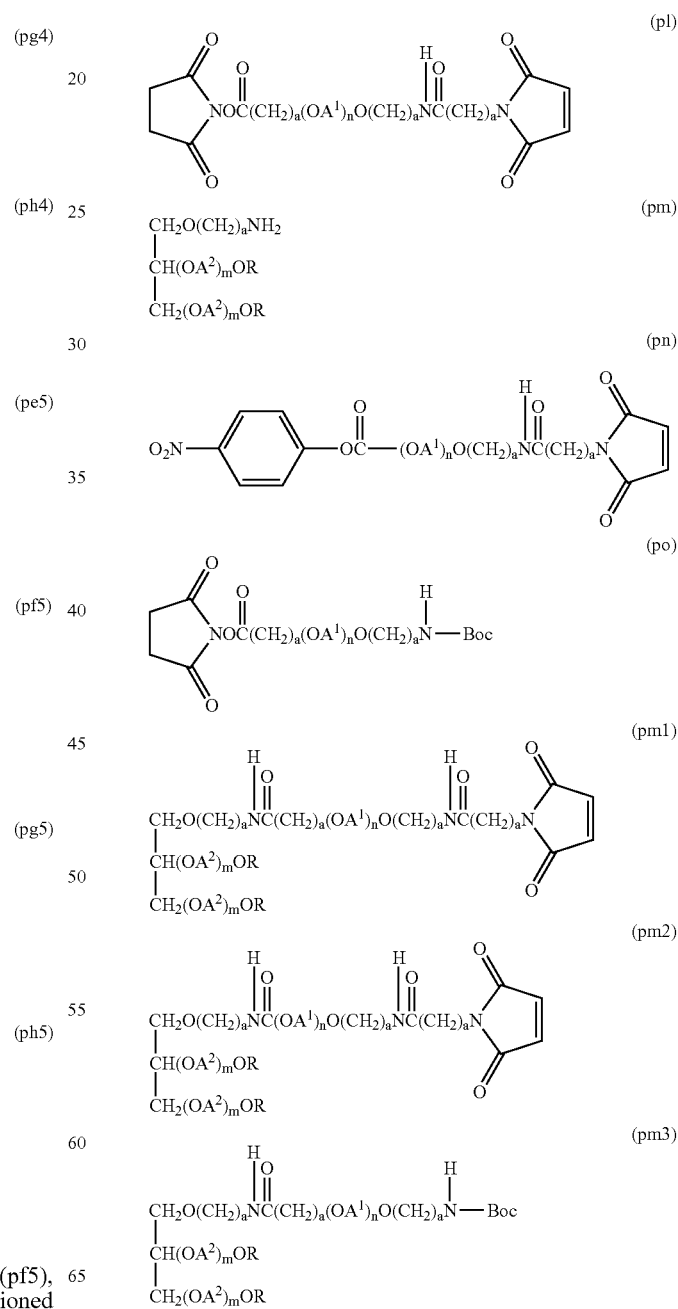

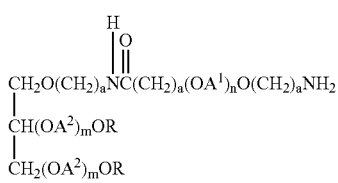

(pm4)

In the formulae (pl), (pm), (pn), (po), (pm1), (pm2), (pm3), and (pm4), R, $OA^2$, $OA^1$, m, n, and a are as mentioned above.

The conditions for the reaction of the compound (pm) with the heterogeneous polyalkylene glycol derivative (pl) or (po) having a succimimide ester group are the same as those in the process for obtaining the above functional group (b). The conditions for the reaction of the compound (pm) with the heterogeneous polyalkylene glycol derivative (pn) having a p-nitrophenylcarbonate group are the same as the conditions of the reaction of the formula (pe) with the formula (pi) mentioned above. The deprotection process for obtaining (pm4) from (pm3) can be achieved through synthesis by a known method. The resulting amine compound (pm4) can be further converted into the maleimide compound (b) or the succinimide ester compound (c).

The polyalkylene glycol derivative having each functional group of the group (I) can be reacted with a bio-related substance but in some cases, the derivative can be further reacted with another compound to produce the other polyalkylene glycol derivative, which can be reacted with a bio-related substance. For example, a polyalkylene glycol derivative of (b) can be synthesized using a polyalkylene glycol derivative having a functional group (a) belonging to the group (I) as a starting material. Also, a polyalkylene glycol derivative of (c) can be synthesized using a polyalkylene glycol derivative having a functional group (h) as a starting material.

In the polyalkylene glycol derivative represented by the formula (1) thus obtained, an amount of ionic functional group-containing impurities other than the target compound, i.e., reactive impurities is 2% or less, more preferably 1% or less, further preferably 0.5% or less in a chromatogram obtained by analysis by liquid chromatography using an ion-exchange column.

Figure 3:
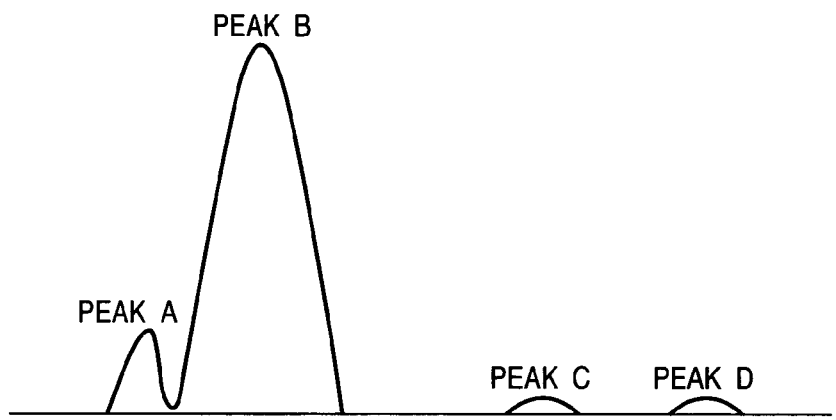
FIG. 3 is a model chart of a chromatogram obtained by liquid chromatography using an ion-exchange column.

FIG. 3 is a model chart of a chromatogram obtained by liquid chromatography using an ion-exchange column.

In the liquid chromatography using an ion-exchange column, a molecule may interact with the column depending on the charge of the molecule and a molecule having a larger charge elutes more slowly. Namely, in FIG. 3, a first eluting peak A shows a compound having a non-ionic functional group, a peak B shows a target compound, a peak C shows a reactive impurity having a molecular weight 0.5 time that of the target compound, and a peak D shows a bifunctional reactive impurity having the same molecular weight as that of the target compound. Namely, in the chromatogram of FIG. 3, impurities having ionic functional group other than the target compound are shown by the peaks C and D.

Accordingly, the amount (%) of the ionic functional group-containing impurities other than the target compound is calculated by the following expression.

(Area of peak C+Area of peak D)/(Total peak area)× 100

In the case that an elution position is unknown, the compound can be suitably identified using an authentic sample.

In the case that the target compound has no ionic functional group, the compound is measured after it is reacted with a labeling agent having an ionic functional group. For example, in the case of (b) in the group I, it can be measured after labeled by the reaction with mercaptopropionic acid to convert the functional group into a carboxyl group. Moreover, in the case of (d) in the group (I), it can be also measured after labeled by the reaction with glycine to convert the functional group into a carboxyl group. Furthermore, in the case of (j) in the group (I), it can be also measured after labeled by the reaction with p-aminobenzoic acid to convert the functional group into a carboxyl group.

When the amount of the reactive impurities is larger than 2%, a reaction product with a bio-related substance becomes heterogeneous, which influences performance of the resulting modified bio-related substance.

In the invention, the liquid chromatography using an ion-exchange column is measured under the following conditions:

(In the Case that an Amine Compound in the Group I (a) is Measured)

HPLC apparatus: Alliance2695 (Nihon Waters K.K.); column: TSK-gel SP-5PW (manufactured by Tosoh Corporation); eluent: sodium phosphate buffer solution (pH 6.5); column temperature: 40° C.; flow rate: 0.5 ml/min; detector: differential refractometer detector (RI) (Nihon Waters K.K.); sample concentration: 5 mg/ml; injection amount: 20 μl.

(In the Case that a Carboxyl Compound in the Group I (h) is Measured)

HPLC apparatus: Alliance2695 (Nihon Waters K.K.); column: ES-502N (Asahipak); eluent: ammonium formate buffer solution (pH 8.0); column temperature: 30° C.; flow rate: 1.0 ml/min; detector: differentihl refractometer detector (RI) (Nihon Waters K.K.); sample concentration: 10 mg/ml; injection amount: 20 μl.

According to the invention, there can be obtained a polyalkylene glycol derivative having polyalkylene glycol chains at the 2- and 3-positions of the glycerin skeleton and having a reactive group capable of being combined with a bio-related substance at the 1-position through a polyalkylene glycol chain. Moreover, there can be provided a bio-related substance modified with a branched polyaikylene glycol derivative. Since the polyethylene glycol derivative of the invention has a polyalkylene glycol chain as a spacer between the glycerin skeleton and the reactive group, it is expected to show reactivity equal to that of a linear polyethylene glycol derivative. Moreover, steric hindrance owing to the own polyalkylene glycol chains is small as compared with the case of conventional branched polyethylene glycol derivatives wherein a reactive functional group is present at the joint base of the polyalkylene glycol chain. Furthermore, at the reaction with a polypeptide, since chain length of the polyalkylene glycol chain as a spacer can be adjusted according to the kind of the polypeptide, it becomes possible to modify functional groups present even inside the polypeptide, so that improvement of conversion can be expected.

EXAMPLES

The following will describe the present invention more specifically with reference to Examples. In this regard, $^1$H-NMR, GPC, and liquid chromatography were employed for analyzing and identifying the compounds in Examples.

<Method for $^1$H-NMR Analysis>

At $^1$H-NMR analysis, JNM-ECP400 manufactured by Nippon Denshi Datum K.K was employed. The integral values in NMR data are theoretical values.

(Method for GPC Analysis):

At GPC analysis, LC10AVP was employed as a GPC system and measurement was carried out under the following conditions:

column: PLgel MIXED-D (manufactured by Polymer Raboratory) two columns; developing solvent: DMF (containing 10 mM lithium bromide); flow rate: 0.7 mi/min; column temperature: 65° C.; detector: RI; sample amount: I mg/mL, 100 μl.

At analysis of an aldehyde compound, measurement was carried out under the following conditions:

system: Alliance2695 (Nihon Waters K.K.); developing solvent: 100 mM sodium acetate buffer (pH=5.2, containing 0.02% $NaN_3$); flow rate: 0.5 mmin; column: Ultlahydrogel500+Ultlahydrogel250 2 columns; column temperature: 30° C.; detector: RI; sample amount: 5 mg/mL, 20 μl.

In GPC data, analysis values at main peaks which are obtained by cutting elution curves perpendicular to base lines at inflection points to remove high-molecular-weight impurities and low-molecular-weight impurities and analysis values over whole peaks from start points of elution to end points of elution were included.

Mn represents a number average molecular weight, Mw represents a weight average molecular weight, and Mp represents a peak top molecular weight.

(Analytic Method for Liquid Chromatography):

The liquid chromatography using an ion-exchange column is measured under the following conditions:
(In the Case that an Amine Compound is Measured)

HPLC apparatus: Alliance2695 (Nihon Waters K.K.); column: TSK-gel SP-5PW (manufactured by Tosoh Corporation); eluent: sodium phosphate buffer (pH 6.5); column temperature: 40° C.; flow rate: 0.5 ml/min; detector: differential refractometer detector (RI) (Nihon Waters K.K.); sample concentration: 5 mg/ml; injection amount: 20 μl.
(In the Case that a Carboxyl Compound is Measured)

HPLC apparatus: Alliance2695 (Nihon Waters K.K.); column: ES-502N (Asahipak); eluent: ammonium formate buffer (pH 8.0); column temperature: 30° C.; flow rate: 1.0 ml/min; detector: differential refractometer detector (I) (Nihon Waters K.K.); sample concentration: 10 mg/ml; injection amount: 20 μl.

Example 1

Synthesis of Compound (p) (Synthesis of R=Methyl Group, $A^2O$=Oxyethylene Group, m=223, and m=475)

Example 1-1

To a 1000 ml round-bottom flask fitted with a thermometer, a nitrogen-introducing tube, and a stirrer were added 132.2 g (1.0 mol) of 2,2-dimethyl-1,3-dioxolane-4-methanol, 202.5 g (1.05 mol) of a 28% methanol solution of sodium methoxide, and 600 ml of toluene. With introducing nitrogen thereinto, the toluene was refluxed under reduced pressure for 1 hour to remove the methanol by distillation. With maintaining the solution at 80° C., 126.6 g (1.0 mol) of benzyl chloride was added dropwise over a period of 2 hours using a dropping funnel, followed by further 2 hours of reaction. After completion of the reaction, the temperature was lowered to 60° C. and 10 g of KYOWAAD 600 was added thereto, followed by 1 hour of stirring. The reaction liquid was filtrated, the solvent was removed, and the residue was purified by distillation (b.p. 93-95° C./266 Pa) to obtain 4-(benzyloxymethyl)-2,2-dimethyl-1,3-dioxolane.

$^1$H-NMR (CDCl$_3$, internal standard: TMS) δ(ppm): 1.36, 1.42 (3H, 3H, s, C(CH$_3$)$_2$), 3.45-3.57 (2H, m, CH$_2$O—C(CH$_3$)$_2$), 3.73-3.76 (1H, m, CHO—C(CH$_3$)$_2$), 4.03-4.07, 4.28-4.32 (2H, m, CH$_2$O—CH$_2$Ph), 4.57 (2H, q, —CH$_2$Ph), 7.15-7.40 (5H, m, —CH$_2$Ph)
(Ph Represents a Phenyl Group)

Example 1-2

To 222 g (1.0 mol) of 4-(benzyloxymethyl)-2,2-dimethyl-1,3-dioxolane was added 350 g of distilled water, and the whole was adjusted to pH 2 with phosphoric acid. With introducing nitrogen thereinto, the solution was heated to 70° C. After 2 hours of reaction, the solution was adjusted to pH 7.0 with sodium hydroxide. After 1 L of chloroform was added thereto and extraction was effected, the resulting chloroform layer was dried over magnesium sulfate and concentrated and the resulting salts were removed by filtrating the condensate to obtain a compound (pa) which was 3-benzyloxy-1,2-propanediol.

$^1$H-NMR (CDCl$_3$, internal standard: TMS) o(ppm): 3.50-3.71 (4H, m, CH$_2$OH, CH$_2$O—CH$_2$Ph), 3.86-3.91 (1H, m, CHOH), 4.54 (2H, m, —CH$_2$Ph), 7.27-7.38 (5H, m, —CH$_2$Ph).

Example 1-3

To a 300 ml round-bottom flask fitted with a thermometer, a nitrogen-introducing tube, a stirrer, and a pressure-reducing line were added 27.3 g (0.15 mol) of 3-benzyloxy-1,2-propanediol, 200 g of dry toluene, and 0.76 g of sodium. With introducing nitrogen thereinto, the whole was heated to 35° C. to dissolve sodium. The solution was charged into a 5 L autoclave thoroughly dried beforehand and the atmosphere was replaced by nitrogen, followed by heating to 100° C. Then, 3100 g of ethylene oxide was added thereto at 100 to 150° C. under a pressure of 1 MPa or lower, followed by continuation of the reaction for another 1.5 hours. Unreacted ethylene oxide gas and toluene were removed by distillation under reduced pressure, and then the whole was cooled to 70° C. After 2.0 kg of the reaction liquid was taken out of the autoclave, the liquid was adjusted to pH 7.5 with 85% aqueous phosphoric acid solution to obtain the following compound (p1).

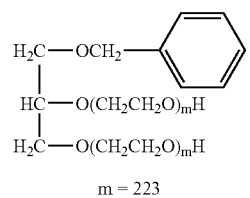

(p1)

m = 223

$^1$H-NMR (CDCl$_3$, internal standard: TMS) δ(ppm): 3.40-3.80 (1789H, m, —CH$_2$O(CH$_2$CH$_2$O)$_m$H, CHO(CH$_2$CH$_2$O)$_m$H, CH$_2$OCH$_2$Ph), 4.54 (2H, s, —CH$_2$Ph), 7.27-7.38 (5H, m, —CH$_2$Ph).

Example 1-4

Into a 2 L round-bottom flask fitted with a thermometer, a nitrogen-introducing tube, a stirrer, a Dean-stark tube, and a condenser tube were added 200 g (10 mmol) of the above compound (p1) and 1000 g of toluene, and the whole was heated under reflux to effect azeotropic removal of 200 g of toluene and water. After cooling to room temperature, 4.05 g (40 mmol) of triethylamine was added thereto and, after heating to 40° C., 3.44 g (30 mmol) of methanesulfonyl chloride was added dropwise thereto, followed by 3 hours of reaction at 40° C. After the reaction was finished, 19.28 g (50 mmol) of 28% methanol solution of sodium methoxide was added thereto, followed by 3 hours of reaction at 40° C. The pressure was reduced with maintaining the reaction liquid at 40° C. and about 200 g of a mixed liquid of methanol/toluene was removed by evaporation, and then salts were removed by filtration. Then, 500 g of toluene was added to the filtrate and the resulting filtrate was transferred into a 2 L round-bottom flask fitted with a thermometer, a nitrogen-introducing tube, a stirrer, a Dean-stark tube, and a condenser tube, followed by heating under reflux to effect azeotropic removal of 200 g of toluene and water. After cooling to room temperature, 4.05 g (40 mmol) of triethylamine was added thereto and, after heating to 40° C., 3.44 g (30 mmol) of methanesulfonyl chloride was again added dropwise thereto, followed by 3 hours of reaction at 40° C. After completion of the reaction, 19.28 g (100 mmol) of 28% methanol solution of sodium methoxide was added thereto, followed by 3 hours of reaction at 40° C. The pressure was reduced with maintaining the reaction liquid at 40° C. and about 200 g of a mixed liquid of methanoV-toluene was removed by distillation, followed by removal of salts by filtration. The filtrate was heated to 50° C. and 200 g of 25% aqueous sodium chloride solution was added thereto. After stirring, the whole was left on standing to separate into layers and the lower water layer was removed. This operation of washing with water was repeated twice. The upper toluene layer was dried over magnesium sulfate and then filtrated and 1 L of ethyl acetate was added to the filtrate. Hexane was added thereto until crystals were precipitated. The crystals were collected by filtration and dried to obtain the following compound (p2).

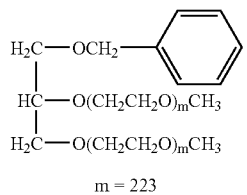

m = 223

$^1$H-NMR (CDCl$_3$, internal standard: TMS) δ(ppm): 3.38 (6H, s, —CH$_3$), 3.40-3.80 (1789H m, —CH$_2$O(CH$_2$CH$_2$O)$_m$CH$_3$, CHO(CH$_2$CH$_2$O)$_m$CH$_3$, CH$_2$OCH$_2$Ph), 4.54 (2H, s, —CH$_2$Ph), 7.27-7.38 (5H, r, —CH$_2$Ph).

Example 1-5

Water removal of palladium carbon was carried out by adding 120 g of 5% palladium carbon (50% hydrous product, manufactured by N. E. M. Cat.) into a pressure filter and replacing the solvent by 500 ml of dry methanol four times with replacement of the atmosphere by nitrogen. Into a 2 L round-bottom flask fitted with a thermometer, a nitrogen-introducing tube, a stirrer, and a condenser tube were added 100 g of the above compound (p2), and the whole amount of the palladium-carbon subjected to solvent replacement. After the replacement by nitrogen, 1200 ml of dry methanol and 500 ml of cyclohexene were added thereto and the whole was heated to 30° C. to be allowed to react for 3.5 hours. The reaction liquid was filtrated and the filtrate was concentrated. Then, 1 L of ethyl acetate was added and hexane was added thereto until crystals were precipitated. The resulting crystals were collected by filtration and dried to obtain the following compound (p3).

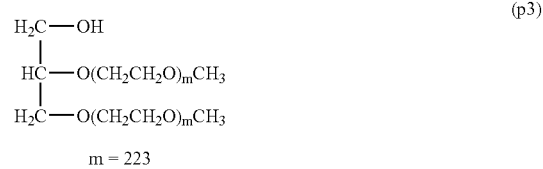

m = 223

$^1$H-NMR (CDCl$_3$, internal standard: TMS) δ(ppm): 3.38 (6H, s, —CH$_3$), 3.40-3.80 (1789H, m, —CH$_2$O(CH$_2$CH$_2$O)$_m$CH$_3$, CHO(CH$_2$CH$_2$O)$_m$CH$_3$, CH$_2$OH).

Example 1-6

In Example 1-3, the autoclave where about 1 kg of the reaction liquid remained was replaced with nitrogen and was heated to 120° C. Then, 1190 g of ethylene oxide was added thereto at 100 to 150° C. under a pressure of 1 MPa or lower, followed by continuation of the reaction for another 4 hours. After completion of the reaction, unreacted ethylene oxide gas was removed with introducing nitrogen gas into a reaction liquid and then the whole was cooled to 80° C. and the liquid was adjusted to pH 7.5 with 85% aqueous phosphoric acid solution to obtain the following compound (p4).

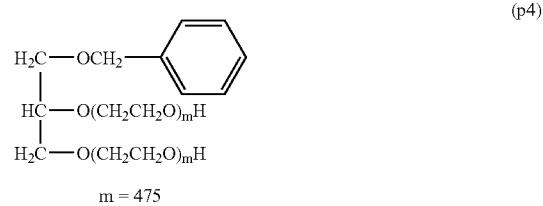

m = 475

$^1$H-NMR (CDCl$_3$, internal standard: TMS) δ(ppm): 3.40-3.80 (3805H, m, —CH$_2$O(CH$_2$CH$_2$O)$_m$H, CHO(CH$_2$CH$_2$O)$_m$H, CH$_2$OCH$_2$Ph), 4.54 (2H, s, —CH$_2$Ph), 7.27-7.38 (5H, m, —CH$_2$Ph).

Example 1-7

Into a 2 L round-bottom flask fitted with a thermometer, a nitrogen-introducing tube, a stirrer, a Dean-stark tube: and a condenser tube were added 252 g (6 mmol) of the above compound (p4) and 1000 g of toluene, and the whole was heated under reflux to effect azeotropic removal of 200 g of toluene and water. After cooling to room temperature, 2.43 g (24 mmol) of triethylamine was added thereto and, after heating to 40° C., 2.06 g (18 mmol) of methanesulfonyl chloride was added dropwise thereto, followed by 3 hours of reaction at 40° C. After completion of the reaction, 6.94 g (36 mmol) of 28% methanol solution of sodium methoxide was added thereto, followed by 3 hours of reaction at 40° C. The pressure was reduced with maintaining the reaction liquid at 40° C. and about 200 g of a mixed liquid of methanoltoluene was removed by distillation, followed by removal of salts by filtration. Then, 500 g of toluene was added to the resulting filtrate and the resulting mixture was transferred into a 2 L round-bottom flask fitted with a thermometer, a nitrogen-introducing tube, a stirrer, a Dean-stark tube, and a condenser tube, followed by heating under reflux to effect azeotropic removal of 200 g of toluene and water. After cooling to room temperature, 2.43 g (24 mmol) of triethylamine was added thereto and, after heating to 40° C., 2.06 g (18 mmol) of methanesulfonyl chloride was again added dropwise thereto, followed by 3 hours of reaction at 40° C. After completion of the reaction, 6.94 g (36 mmol) of 28% methanol solution of sodium methoxide was added thereto, followed by 3 hours of reaction at 40° C. The pressure was reduced with maintaining the reaction liquid at 40° C. and about 200 g of a mixed liquid of methanol/toluene was removed by distillation, followed by removal of salts by filtration. The filtrate was heated to 50° C. and 200 g of 25% aqueous sodium chloride solution was added thereto. After stirring, the whole was left on standing to separate into layers and the lower water layer was removed. This operation of washing with water was repeated twice. The upper toluene layer was dried over magnesium sulfate and then filtrated and 1 L of ethyl acetate was added to the filtrate. Hexane was added thereto until crystals were precipitated. The crystals were collected by filtration and dried to o6tain the following compound (p5).

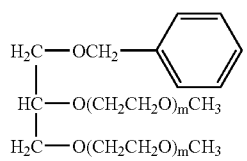

m = 475

$^1$H-NMR (CDCl$_3$, internal standard: TMS) δ(ppm): 3.38 (6H, s, —C$\underline{H}_3$), 3.40-3.80 (3805H, m, —C$\underline{H}_2$O(C$\underline{H}_2$C$\underline{H}_2$O)$_m$CH$_3$, C$\underline{H}$O(C$\underline{H}_2$C$\underline{H}_2$O)$_m$CH$_3$, C$\underline{H}_2$OCH$_2$Ph), 4.54 (2H, s, —C$\underline{H}_2$Ph), 7.27-7.38 (5H, m, —CH$_2$P$\underline{h}$).

Example 1-8

Water removal of palladium carbon was carried out by adding 200 g of 5% palladium carbon (50% hydrous product, manufactured by N. E. M. Cat.) into a pressure filter and replacing the solvent by 500 ml of dry methanol four times with replacement of the atmosphere by nitrogen. Into a 2 L round-bottom flask fitted with a thermometer, a nitrogen-introducing tube, a stirrer, and a condenser tube were added 100 g of the above compound (p5) and the whole amount of the palladium-carbon subjected to solvent replacement. After the replacement by nitrogen, 1200 ml of dry methanol and 500 ml of cyclohexene were added thereto and the whole was heated to 30° C. to be allowed to react for 3.5 hours. The reaction liquid was filtrated and the filtrate was concentrated. Then, 1 L of ethyl acetate was added and hexane was added thereto until crystals were precipitated. The resulting crystals were collected by filtration and dried to obtain the following compound (p6).

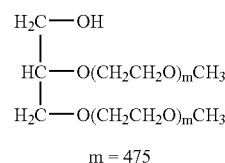

m = 475

$^1$H-NMR (CDCl$_3$, internal standard: TMS) δ(ppm): 3.38 (6H, s, —C$\underline{H}_3$), 3.40-3.80 (3805H, m, —C$\underline{H}_2$O(C$\underline{H}_2$C$\underline{H}_2$O)$_m$CH$_3$, C$\underline{H}$O((C$\underline{H}_2$C$\underline{H}_2$O)$_m$CH$_3$, C$\underline{H}_2$OH).

Example 2

Synthesis of Compound (pd) (Synthesis of R=Methyl Group, A$^2$O, A$^1$O=Oxyethylene Group, m=223, n=38, and Synthesis of m=475, n=46)

Example 2-1

Into a 3 L four-neck flask fitted with a thermometer, a nitrogen-introducing tube, a stirrer, and a pressure-reducing line were added 300 g of the compound (p3) and 1100 g of toluene, and the whole was heated under reflux to effect azeotropic removal of water. After the reaction liquid was cooled to 40° C., 1.31 g of a 28% methanol solution of sodium methoxide was added thereto. The reaction liquid was maintained at 75 to 80° C. with nitrogen bubbling under normal pressure for 25 minutes and subsequently, 156 g of a mixed solution of methanol/toluene was removed by distillation under slightly reduced pressure with stirring for 60 minutes. After the reaction liquid was cooled to room temperature, the solution was charged into a 5 L autoclave which had been thoroughly dried beforehand and the atmosphere was replaced by nitrogen, followed by heating the whole to 90 to 100° C. with nitrogen bubbling for 25 minutes to remove 137 g of toluene by distillation. Then, 30 ml of ethylene oxide was added thereto at 100 to 150° C. under a pressure of 1 MPa or lower, followed by continuation of the reaction for another 8 hours. Unreacted ethylene oxide gas and toluene were removed by distillation under reduced pressure, then the whole was cooled to 70° C., and the reaction liquid was adjusted to pH 7.5 with a 85% aqueous phosphoric acid solution to obtain the following compound (p7).

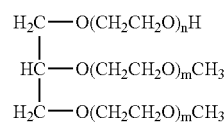

m = 223 n = 38

$^1$H-NMR (CDCl$_3$, internal standard: TMS) δ(ppm): 3.38 (6H, s, —C$\underline{H}_3$), 3.40-3.80 (1941H, m, —C$\underline{H}_2$O(C$\underline{H}_2$C$\underline{H}_2$O)$_m$CH$_3$, C$\underline{H}$O(C$\underline{H}_2$C$\underline{H}_2$O)$_m$CH$_3$, —C$\underline{H}_2$O(C$\underline{H}_2$C$\underline{H}_2$O)$_n$OH).

Example 2-2

Into a 5 L four-neck flask fitted with a thermometer, a nitrogen-introducing tube, a stirrer, and a pressure-reducing line were added 827 g of the compound (p6) and 2000 g of toluene, and the whole was heated under reflux to effect azeotropic removal of water. After the reaction liquid was cooled to 60° C., 1.01 g of a 28% methanol solution of sodium methoxide was added thereto. The reaction liquid was maintained at 70 to 75° C. with nitrogen bubbling under normal pressure for 30 minutes and subsequently, 102 g of a mixed solution of methanol/toluene was removed by distillation under slightly reduced pressure with stirring for 60 minutes. After the reaction liquid was cooled to room temperature, the solution was charged into a 5 L autoclave which had been thoroughly dried beforehand and the atmosphere was replaced by nitrogen, followed by heating the whole to 90 to 100° C. with nitrogen bubbling for 20 minutes to remove 92 g of toluene by distillation. Then, 40 ml of ethylene oxide was introduced thereto at 100 to 150° C. under a pressure of 1 MPa or lower, followed by continuation of the M reaction for another 11.5 hours. Unreacted ethylene oxide gas and toluene were removed by distillation under reduced pressure, then the whole was cooled to 70° C., and the reaction liquid was adjusted to pH 7.5 with a 85% aqueous phosphoric acid solution to obtain the following compound (p8).

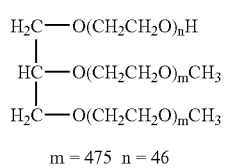

m = 475  n = 46

$^1$H-NMR (CDCl$_3$, internal standard: TMS) δpm): 3.38 (6H, s, —C$\underline{H_3}$), 3.40-3.80 (3989H, m, —C$\underline{H_2}$O(C$\underline{H_2}$C$\underline{H_2}$O)$_m$CH$_3$, C$\underline{H}$O(C$\underline{H_2}$C$\underline{H_2}$O)$_m$CH$_3$, —C$\underline{H_2}$O(C$\underline{H_2}$C$\underline{H_2}$O)$_n$OH).

Example 3

Synthesis of Aldehyde Compound (Group 1(j)) (R=Methyl Group, A$^2$O, A$^1$O=Oxyethylene Group, m=475, n=46)

Example 3-1

Into a 500 ml four-neck flask fitted with a thermometer, a nitrogen-introducing tube, and a stirrer were charged 50 g of the compound (p8), 0.050 g of BHT, and 300 g of toluene, and the whole was heated under reflux to effect azeotropic removal of water. After the reaction liquid was cooled to 40° C., 0.358 g of triethylamine and 0.325 g of methanesulfonyl chloride were added thereto, followed by 5 hours of mesylation reaction at 40° C. Into another 300 ml four-neck flask fitted with a thermometer, a nitrogen-introducing tube, and a stirrer were added 22.1 g of 3,3-diethoxy-1-propanol and 202 g of toluene, and the whole was heated under reflux to effect azeotropic removal of water. After the reaction liquid was cooled to 30° C., 0.66 g of sodium was added and the whole was stirred at room temperature until it was dissolved. After dissolution of the sodium was confirmed, the whole amount of the dissolved liquid was added to the mesylation reaction liquid, followed by 3 hours of reaction at 70° C. After completion of the reaction, 540 μl of ion-exchange water was added and the whole was further stirred at 70° C. for 30 minutes. After filtration of the reaction liquid, 1000 ml of ethyl acetate was added to the filtrate, and 1000 ml of hexane was added to precipitate crystals. The crystals were dissolved under heating with adding 1000 ml of ethyl acetate, and 1000 ml of hexane was added to precipitate crystals. The crystals were collected by filtration and dried to obtain the following acetal compound (p9).

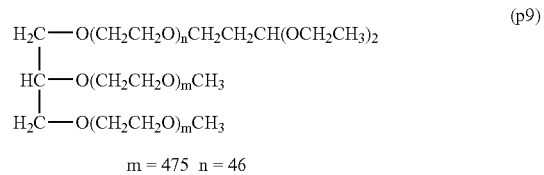

m = 475  n = 46

$^1$H-NMR (CD$_3$OD, internal standard: TMS) δ(ppm): 1.18 (6H, t, —CH$_2$CH$_2$CH(OCH$_2$C$\underline{H_3}$)$_2$), 1.82-1.86 (2H, m, —CH$_2$C$\underline{H_2}$CH(OCH$_2$CH$_3$)$_2$), 3.38 (6H, s, —C$\underline{H_3}$), 3.40-3.80 (3995H, m, —C$\underline{H_2}$O(C$\underline{H_2}$C$\underline{H_2}$O)$_m$CH$_3$, C$\underline{H}$O(C$\underline{H_2}$C$\underline{H_2}$O)$_m$CH$_3$, —C$\underline{H_2}$O(C$\underline{H_2}$C$\underline{H_2}$O)$_n$CH$_2$CH$_2$CH(OC$\underline{H_2}$CH$_3$)$_2$), 4.65 (1H, t, —CH$_2$C$\underline{H_2}$C$\underline{H}$(OCH$_2$CH$_3$)$_2$).

Example 3-2

Into a 3 L beaker was weighed 43 g of the resulting acetal compound (p9). Then, 817 g of water for injection was added to dissolve the crystals. After dissolution, the solution was adjusted to pH 1.5 with 85% phosphoric acid, followed by 2 hours of stirring at room temperature with nitrogen bubbling under light shielding. Thereafter, the solution was adjusted to pH 6.7 with 30% aqueous sodium hydroxide solution and 172 g of sodium chloride was added and dissolved. The whole was adjusted to pH 7.0 with 30% aqueous sodium hydroxide solution, followed by two times of chloroform extraction. The resulting chloroform layer was dried over magnesium sulfate and, after filtration, chloroform was removed by distillation to effect concentration. The concentrate was dissolved under heating with adding 300 ml of ethyl acetate, and 300 ml of hexane was added to precipitate crystals. The crystals was collected by filtration and dried to obtain the following aldehyde compound (p10).

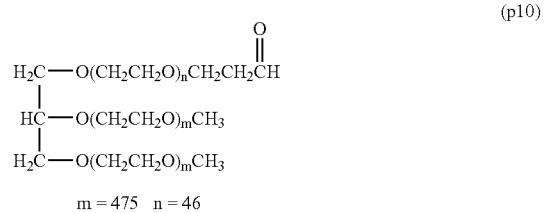

m = 475  n = 46

$^1$H-NM (CDCl$_3$, internal standard: TMS) δ(ppm): 2.66-2.69 (2H, m, C$\underline{H_2}$COH), 3.38 (6H, s, —C$\underline{H_3}$, 3.40-3.80 (3991H, m, —C$\underline{H_2}$O(C$\underline{H_2}$C$\underline{H_2}$O)$_m$CH$_3$, C$\underline{H}$O(C$\underline{H_2}$C$\underline{H_2}$O)$_m$CH$_3$, —C$\underline{H_2}$O(C$\underline{H_2}$C$\underline{H_2}$O)$_n$C$\underline{H_2}$CH$_2$COH), 9.79 (1H. t, —CH$_2$CH$_2$COH).

<main peak> number average molecular weight (Mn): 43175, weight average molecular weight (Mw): 44380, polydispersity (Mw/Mn): 1.028, peak top molecular weight (Mp): 45539;

<whole peak> number average molecular weight (Mn): 40512, weight average molecular weight (Mw): 42910, polydispersity (Mw/Mn): 1.059, peak top molecular weight (Mp): 45288.

Low-molecular-weight impurities: 4.78%.

Example 3-3

Twenty miligrams of the compound of the formula (p10) was weighed and dissolved in 2 ml of 0.1M sodium acetate buffer solution (pH=4.0). To the solution was added 68 μl of a methanol solution (40 mg/ml) of p-aminobenzoic acid prepared separately. Furthermore, 128 µl of 10 mg/ml aqueous solution of sodium cyanoborohydride prepared separately was added thereto, followed by 2 hours of reaction at 75° C. To a gel filtration column equilibrated with 0.3 mM ammonium formate buffer solution was added the whole amount of the reaction solution. Furthermore, the buffer solution was added thereto and a high-molecular-weight fraction which was first eluted was collected into a vial for HPLC measurement. When the fraction was analyzed by liquid chromatography (concentration of ammonium formate buffer solution: 0.3 mM), ionic functional group-containing impurities other than the aimed compound were detected in an amount of 0.88%.

Example 4

Synthesis of Aldehyde Compound (Group I(j)) (R=Methyl Group, $A^2O$, $A^1O$=Oxyethylene Group, m=223, n=38)

Example 4-1

Into a 500 ml four-neck flask fitted with a thermometer, a nitrogen-introducing tube, and a stirrer were charged 70 g of the compound (p7), 0.070 g of BHT, and 350 g of toluene, and the whole was heated under reflux to effect azeotropic removal of water. After the reaction liquid was cooled to 40° C., 0.695 g of triethylamine and 0.656 g of methanesulfonyl chloride were added thereto, followed by 3 hours of mesylation reaction at 40° C. A sodium salt solution of 3,3-diethoxy-1-propanol was added to the mesylation reaction liquid so that sodium equivalent is 6 equivalents, followed by 3 hours of reaction at 70° C. After completion of the reaction, 400 µl of ion-exchange water was added and the whole was further stirred at 70° C. for 30 minutes. After filtration of the reaction liquid, 1500 ml of ethyl acetate was added to the filtrate, and 1500 ml of hexane was added to precipitate crystals. The crystals were collected by filtration and dissolved under heating with adding 1500 ml of ethyl acetate, and 1500 ml of hexane was added to precipitate crystals. The crystals were collected by filtration and dried to obtain the following acetal compound (p11).

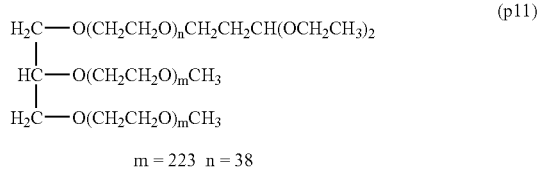

m = 223  n = 38

$^1$H-NMR (CD$_3$OD, internal standard: TMS) δ(ppm): 1.18 (6H, t, —CH$_2$CH$_2$CH(OCH$_2$CH$_3$)$_2$), 1.82-1.86 (2H, m, —CH$_2$CH$_2$CH(OCH$_2$CH$_3$)$_2$), 3.38 (6H, s, —CH$_3$), 3.40-3.80 (1947H, m, —CH$_2$O(CH$_2$CH$_2$O)—CH$_3$, CHO(CH$_2$CH$_2$O)$_m$CH$_3$, —CH$_2$O(CH$_2$CH$_2$O)$_n$CH$_2$CH$_2$CH(OCH$_2$CH$_3$)$_2$), 4.65 (1H, t, —CH$_2$CH$_2$CH(OCH$_2$CH$_3$)$_2$).

Example 4-2

Using the resulting acetal compound (p11), the following aldehyde compound (p12) was obtained in a similar manner to Example 3-2.

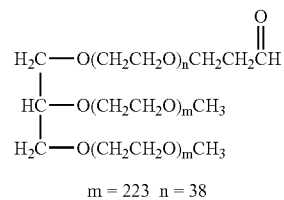

m = 223  n = 38

$^1$H-NMR (CDCl$_3$, internal standard: TMS) δ(ppm): 2.67-2.70 (2H, m, CH$_2$COH), 3.38 (6H, 5, —CH$_3$, 3.40-3.80 (1943H, m, —CH$_2$O(CH$_2$CH$_2$O)$_m$CH$_3$, CHO(CH$_2$CH$_2$O)$_m$CH$_3$, —CH$_2$O(CH$_2$CH$_2$O)$_n$CH$_2$CH$_2$COH), 9.79 (1H, t, —CH$_2$CH$_2$COH).

<main peak> number average molecular weight (Mn): 21392, weight average molecular weight (Mw): 21178, polydispersity (Mw/Mn): 1.022, peak top molecular weight (Mp): 21392;

<whole peak> number average molecular weight (Mn): 20155, weight average molecular weight (Mw): 20924, polydispersity (Mw/Mn): 1.038, peak top molecular weight (Mp): 21392.

Low-molecular-weight impurities: 3.86%.

Example 4-3

Twenty miligrams of the compound of the formula (p12) was weighed and dissolved in 2 ml of 0.1M sodium acetate buffer solution (pH=4.0). To the solution was added 68 µl of a methanol solution (40 mg/ml) of p-aminobenzoic acid prepared separately. Furthermore, 128 µl of 10 mg/ml aqueous solution of sodium cyanoborohydride prepared separately was added thereto, followed by 2 hours of reaction at 75° C. To a gel filtration column equilibrated with 1.5 mM ammonium formate buffer solution was added the whole amount of the reaction solution. Furthermore, the buffer solution was added thereto and a high-molecular-weight fraction which was first eluted was collected into a vial for HPLC measurement. When the fraction was analyzed by liquid chromatography (concentration of ammonium formate buffer solution: 1.5 mM), ionic functional group-containing impurities other than the aimed compound were detected in an amount of 0.68%.

Example 5

Synthesis of Amino Compound (Group I(a)) (R=Methyl Group, $A^2O$, $A^1O$=Oxyethylene Group, m=475, n=46)

Example 5-1

Into a 500 ml round-bottom flask fitted with a thermometer, a nitrogen-introducing tube, a stirrer, and a condenser tube was added 50 g of the compound (p8). Then, 50 g of ion-exchanged water and 3.3 g of 50% aqueous potassium hydroxide solution were added thereto, and the whole was heated to 40° C. to dissolve them with nitrogen bubbling. After dissolution, the solution was cooled to 10° C. or lower and 146 g of acrylonitrile was added dropwise over a period of 2 hours with maintaining a temperature of 5 to 10° C. After the dropwise addition, the reaction was continued for another 2 hours. The nitrogen bubbling was continued during the reaction. Then, 19.5 g of 8.5% aqueous phosphoric acid solution was added dropwise, followed by neutralization of the reaction liquid. Subsequently, 90 g of ion-exchanged water, 116 g of ethyl acetate, and 12 g of hexane were added to the reaction liquid and, after 10 minutes of stirring, the whole was left on standing for 20 minutes. The upper ethyl acetate layer was removed with suction by means of a peristaltic pump. Subsequently, 116 g of ethyl acetate was added thereto and, after stirred for 10 minutes, the whole was left on standing for 20 minutes. The upper ethyl acetate layer was removed with suction by means of a peristaltic pump. The extraction with ethyl acetate was repeated eight times. After completion of the extraction, 31 g of sodium chloride was added to the aqueous layer and dissolved therein, and then the solution was extracted with 300 g of chloroform. The resulting chloroform layer was dried over magnesium sulfate, filtrated, and then concentrated. Thereafter, 460 g of ethyl acetate was added to the concentrate, which was dissolved therein. Then, hexane was added thereto until crystals were precipitated. The crystals were collected by filtration and dried to obtain the following nitrile compound (p13).

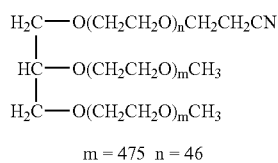

(p13)

m = 475  n = 46

$^1$H-NMR (CDCl$_3$, internal standard: TMS) δ(ppm): 2.59-2.66 (2H, m, —C$\underline{H_2}$CH$_2$CN), 3.38 (6H, s, —C$\underline{H_3}$), 3.40-3.80 (3991H, m, —C$\underline{H_2}$O(C$\underline{H_2}$C$\underline{H_2}$O)$_m$CH$_3$, C$\underline{H}$O(C$\underline{H_2}$C$\underline{H_2}$O)$_m$CH$_3$, C$\underline{H_2}$O(C$\underline{H_2}$C$\underline{H_2}$O)$_n$CH$_2$C$\underline{H_2}$CN).

Example 5-2

To a 1 L autoclave were added 27 g of the nitrile compound of the formula (p13), 410 g of toluene, and 2.43 g of nickel (manufactured by N. E. M. Cat., 5136p). After replacement of the atmosphere with nitrogen, the autoclave was pressurized with nitrogen until the inner pressure reached 0.3 MPa. Subsequently, after heated to 60° C., the autoclave was charged with ammonia gas until the inner pressure reached 0.4 MPa, and then pressurized with hydrogen until the inner pressure reached 3.5 MPa. Then, the autoclave was heated to 130° C. and pressurized with hydrogen until the inner pressure reached 4.0 MPa, followed by 3 hours of reaction at 130° C. After completion of the reaction, the reaction liquid was cooled to 70° C., and purge with nitrogen was repeated three times. The whole amount of the reaction liquid was taken out and the mixture was filtrated to remove the nickel catalyst. After the filtrate was concentrated to about 300 ml and cooled to room temperature, hexane was added until crystals were precipitated. The crystals were collected by filtration and dried to obtain the following amine compound (p14).

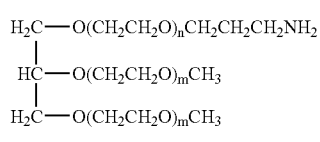

(p14)

m = 475  n = 46

$^1$H-NMR (D$_2$O, internal standard: H$_2$O=4.7ppm) δ(ppm): 1.82-1.90 (2H, m, —CH$_2$C$\underline{H_2}$CH$_2$NH$_2$), 2.90-2.97 (2H, m, —CH$_2$C$\underline{H_2}$CH$_2$NH$_2$), 3.38 (6H, s, —C$\underline{H_3}$), 3.40-3.80 (3991H, m, —C$\underline{H_2}$O(C$\underline{H_2}$C$\underline{H_2}$O)$_m$CH$_3$, C$\underline{H}$O(C$\underline{H_2}$C$\underline{H_2}$O)$_m$CH$_3$, C$\underline{H_2}$O(C$\underline{H_2}$C$\underline{H_2}$O)$_n$CH$_2$CH$_2$CH$_2$NH$_2$).

<main peak> number average molecular weight (Mn): 41882, weight average molecular weight (Mw): 42655, polydispersity (Mw/Mn): 1.018, peak top molecular weight (Np): 43087;

<whole peak> number average molecular weight (Mn): 39452, weight average molecular weight (Mw): 41748, polydispersity (Mw/Mn): 1.058, peak top molecular weight (Mp): 43087.

Low-molecular-weight impurities: 4.26%

Example 5-3

When the compound of the formula (p 14) was analyzed on a liquid chromatography using an ion-exchange column (concentration of sodium phosphate buffer solution: 0.2 mM), ionic functional group-containing impurities other than the target compound were detected in an amount of 0.42%.

Example 6

Synthesis of Succinimide Ester compound (Group I(c)) (R=Methyl Group, A$^2$O, A$^2$O=Oxyethylene Group, m=475, n=46)

Into a 200 ml round-bottom flask fitted with a thermometer, a nitrogen-introducing tube, a stirrer, and a condenser tube were charged 11 g of the compound of the formula (p14), 60 g of dry toluene, 0.011 g of BHT, and 0.11 g of sodium acetate, and the whole was heated to dissolved them. The reaction liquid was heated to 55° C. and 0.239 g of glutaric anhydride was added thereto, followed by 5 hours of reaction at 55° C. Thereafter, the reaction liquid was cooled to 40° C. and then 0.48 g of N-hydroxysuccinimide was added thereto. After 1 hour of stirring, 0.87 g of DCC was added thereto, followed by 4 hours of reaction. After completion of the reaction, the reaction liquid was filtered to remove DCU. Then, 80 g of hexane was added to the filtrate to precipitate crystals and the crystals were collected by filtration. The collected crystals were dissolved under heating with adding 10 g of acetonitrile and 80 g of ethyl acetate. Then, 80 g of hexane was added thereto to precipitate crystals and the crystals were collected by filtration. The crystallization operation was repeated five times and the resulting crystals were dried to obtain the compound of the following (p15).

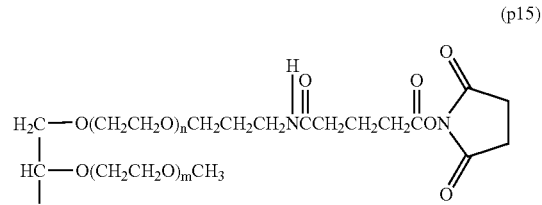

(p15)

m = 475  n = 46

$^1$H-NMR (CDCl$_3$, internal standard: TMS) δ(ppm): 1.76-1.81 (2H, m, —OCH$_2$C$\underline{H_2}$CH$_2$NHCOCH$_2$CH$_2$CH$_2$—), 2.05-2.11 (2H, m, —NHCOCH$_2$C$\underline{H_2}$CH$_2$COON—), 2.29 (2H, t, —NHCOC$\underline{H_2}$CH$_2$CH$_2$COON—), 2.69 (2H, t, —NHCOCH$_2$CH$_2$C$\underline{H_2}$COON—), 2.86 (4H, s, succinimide), 3.38 (6H, s, —C$\underline{H_3}$), 3.40-3.80 (3993H, m, —C$\underline{H_2}$O(C$\underline{H_2}$C$\underline{H_2}$O)$_m$CH$_3$, C$\underline{H}$O(C$\underline{H_2}$C$\underline{H_2}$O)$_m$CH$_3$, C$\underline{H_2}$—O(C$\underline{H_2}$C$\underline{H_2}$O)$_n$C$\underline{H_2}$CH$_2$C$\underline{H_2}$NHCOCH$_2$CH$_2$CH$_2$—).

<main peak> number average molecular weight (Mn): 42022, weight average molecular weight (Mw): 42800, polydispersity (Mw/Mn): 1.019, peak top molecular weight (Mp): 43314;

<whole peak> number average molecular weight (Mn): 39882, weight average molecular weight (Mw): 41973, polydispersity (Mw/Mn): 1.052, peak top molecular weight (Mp): 43314.

Low-molecular-weight impurities: 4.44%

Example 7

Synthesis of Carboxyl Compound (Group 1(h)) (R=Methyl Group, $A^2O$, $A^1O$=Oxyethylene Group, m=475, n=46)

Example 7-1

Into a 500 ml round-bottom flask fitted with a thermometer, a nitrogen-introducing tube, a stirrer, a Dean-stark tube, and a condenser tube were charged 200 g of the compound of the formula (p8), 250 g of toluene, and 0.02 g of BHT, and the whole was heated under reflux at 110° C. or higher to effect azeotropic removal of water. After the reaction liquid was cooled to 40° C., 10 g of potassium hydroxide was added thereto and, after 1 hour of stirring, 4.4 g of ethyl bromohexanoate was added dropwise thereto over a period of 15 minutes with maintaining it at 40° C., followed by 7 hours of stirring. Furthermore, 10 g of potassium hydroxide was added thereto and, after 30 minutes of stirring, 4.4 g of ethyl bromohexanoate was added dropwise thereto over a period of 30 minutes with maintaining it at 40° C., followed by 6 hours of stirring. To the reaction liquid was added 200 g of water for injection, and the whole was heated to 50° C. and then stirred for 2 hours. Subsequently, the reaction mixture was cooled to 10° C. or lower and 49 g of 85% phosphoric acid was slowly added so that temperature of the reaction liquid did not exceed 10° C. To the reaction liquid were added 200 ml of ethyl acetate, 200 ml of hexane, and 0.02 g of BHT, and the whole was stirred for 15 minutes, followed by leaving the mixture on standing until layers separated. After the layer separation, the upper organic layer was removed with suction and 300 ml of chloroform was added to the lower aqueous layer. After 15 minutes of stirring, the whole was left on standing until layers separated. After the layer separation, the lower chloroform layer was taken out and 200 ml of ethyl acetate and 50 g of magnesium sulfate were added to remove water. After the magnesium sulfate was removed by filtration, hexane was added to the filtrate until crystals were precipitated. After the crystals were collected by filtration, the crystals were dissolved under heating in 200 ml of ethyl acetate. After dissolution, the solution was cooled until crystals were precipitated. The crystallization operation was repeated four times and the resulting crystals were dried to obtain the compound of the following (p 16).

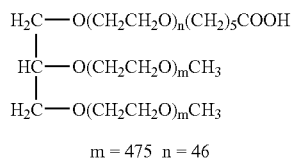

m = 475  n = 46

$^1$H-NMR (CDCl$_3$, internal standard: TMS) δ(ppm): 1.26-1.46 (2H, m, —OCH$_2$CH$_2$CH$_2$CH$_2$CH$_2$COOH), 1.58-1.65 (4H, m, —OCH$_2$CH$_2$CH$_2$CH$_2$CH$_2$COOH), 2.31 (2H, t, —OCH$_2$CH$_2$CH$_2$CH$_2$CH$_2$COOH), 3.38 (6H, s, —CH$_3$) 3.40-3.80 (3987H, m —CH$_2$O(CH$_2$CH$_2$O)$_m$CH$_3$, CHO(CH$_2$CH$_2$O)$_m$CH$_3$, —CH$_2$O(CH$_2$CH$_2$O)$_n$CH$_2$CH$_2$CH$_2$CH$_2$CH$_2$COOH).

<main peak> number average molecular weight (Mn): 41670, weight average molecular weight (Mw): 42445, polydispersity (Mw/Mn): 1.019, peak top molecular weight (Mp): 43040;

<whole peak> number average molecular weight (Mn): 38643, weight average molecular weight (Mw): 40861, polydispersity (Mw/Mn): 1.057, peak top molecular weight (Mp): 43040.

Low-molecular-weight impurities: 4.61%

Example 7-2

When the compound of the formula (p16) was analyzed on a liquid chromatography using an ion-exchange column (concentration of ammonium formate buffer solution: 0.15 mM), ionic functional group-containing impurities other than the target compound were detected in an amount of 0.78%.

Example 8

Synthesis of Succinimide Ester Compound (Group I(c)) (R=Methyl Group, $A^2O$, $A^1O$=Oxyethylene Group, m=475, n=46)

Into a 100 ml round-bottom flask fitted with a thermometer, a nitrogen-introducing tube, a stirrer, and a condenser tube were charged 5 g of the carboxyl compound of the formula (p16), 30 ml of dry toluene, 0.005 g of BHT, and 0.05 g of sodium acetate, and the whole was heated to dissolved them. The reaction liquid was heated to 50° C. and 28 mg of N-hydroxysuccinimide was added thereto. After 1 hour of stirring, the reaction liquid was cooled to 40° C. After cooling, 49 mg of DCC was added thereto, followed by 5 hours of reaction. After completion of the reaction, the reaction liquid was filtered to remove DCU. Then, 50 ml of hexane was added to the filtrate to precipitate crystals and the crystals were collected by filtration. The collected crystals were dissolved under heating with adding 20 ml of acetonitrile and 200 ml of ethyl acetate. Then, 200 ml of hexane was added thereto to precipitate crystals and the crystals were collected by filtration. The crystallization operation was repeated three times and the resulting crystals were dried to obtain the compound of the following (p17).

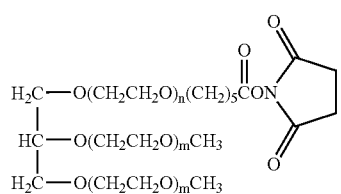

m = 475  n = 46

$^1$H-NMR (CDCl$_3$, internal standard: TMS) δ(ppm): 1.44-1.52 (2H, m, —OCH$_2$CH$_2$CH$_2$CH$_2$CH$_2$COON), 1.59-1.63 (2H, m, —OCH$_2$CH$_2$CH$_2$CH$_2$CH$_2$COON), 1.74-1.81 (2H, m, —OCH$_2$CH$_2$CH$_2$CH$_2$CH$_2$COON), 2.61 (2H, t, —OCH$_2$CH$_2$CH$_2$CH$_2$CH$_2$COON), 2.84 (4H, s, —NHS), 3.38 (6H, s, —CH$_3$), 3.40-3.80 (3991H, m, —CH$_2$O(CH$_2$CH$_2$O)$_m$CH$_3$, CHO(CH$_2$CH$_2$O)$_m$CH$_3$, —CH$_2$O(CH$_2$CH$_2$O)$_n$CH$_2$CH$_2$CH$_2$CH$_2$CH$_2$COON).

<main peak> number average molecular weight (Mn): 42059, weight average molecular weight (Mw): 42837, polydispersity (Mw/Mn): 1.019, peak top molecular weight (Np): 43443;

<whole peak> number average molecular weight (Mn): 39557, weight average molecular weight (Mw): 41790, polydispersity (Mw/Mn): 1.056, peak top molecular weight (Mp): 43443.

Low-molecular-weight impurities: 4.34%

Example 9

Synthesis of Carboxyl Compound (Group 1(h)) (R=Methyl Group, $A^2O$, $A^1O$=Oxyethylene Group, m=475, n=47)

Example 9-1

Into a 500 ml round-bottom flask fitted with a thermometer, a nitrogen-introducing tube, a stirrer, a Dean-stark tube, and a condenser tube were charged 130 g of the compound of the formula (p6) and 420 g of toluene, and the whole was heated at 110° C. or higher to effect azeotropic removal of water. The reaction liquid was cooled to 80° C. and 3.13 g of triethylamine and 4.99 g of p-nitrophenyl chloroformate were added thereto, followed by 5 hours of reaction at 80° C. After the reaction liquid was filtered, 1560 g of ethyl acetate was added and the whole was cooled to 30° C. Thereafter, 780 g of hexane was added to precipitate crystals and the crystals were collected by filtration. The collected crystals were dissolved under heating with adding 1300 g of ethyl acetate. Then, 520 g of hexane was added thereto to precipitate crystals and the crystals were collected by filtration. The crystallization operation was repeated four times and the resulting crystals were dried to obtain the compound of the following (p18).

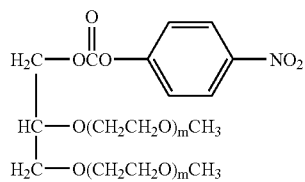

(p18)

m = 475

$^1$H-NMR (CDCl$_3$, internal standard: TMS) δ(ppm): 3.38 (6H, s, —C<u>H</u>$_3$), 3.40-3.80 (4043H, m, —C<u>H</u>$_2$O(C<u>H</u>$_2$C<u>H</u>$_2$O)$_m$CH$_3$, C<u>H</u>O(C<u>H</u>$_2$C<u>H</u>$_2$O)$_m$CH$_3$), 4.34-4.48 (2H, m, —C<u>H</u>$_2$OCOO—Ph—NO$_2$), 7.40, 8.28 (2H, 2H, d, d, —CH$_2$OCOO—<u>Ph</u>—NO$_2$).

Example 9-2

Into a 100 ml screw tube were added 4.3 g of the compound of the following formula (p18), 0.25 g of the heterogeneous polyethylene glycol (n=47) of the following formula (p19), 40 ml of dry toluene, and 0.05 g of triethylamine, followed by 9 hours of reaction at 50° C. To the reaction liquid were added 400 ml of ethyl acetate and 300 ml of hexane to precipitate crystals. After the crystals were collected by filtration, they were again crystallized from 400 ml of ethyl acetate. The resulting crystals were dried to obtain the compound of the following (p20).

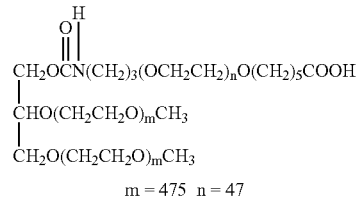

$H_2N(CH_2)_3(OCH_2CH_2)_nO(CH_2)_5COOH$ (p19)
n = 47

(p20)

m = 475  n = 47

$^1$H-NMR (CDCl$_3$, internal standard: TMS) δ(ppm): 1.38-1.46 (2H, m, —OCH$_2$CH$_2$<u>CH</u>$_2$CH$_2$CH$_2$COOH), 1.59-1.67 (4H, m, —OCH$_2$<u>CH</u>$_2$CH$_2$<u>CH</u>$_2$CH$_2$COOH), 1.74-1.80 (2H, m, —OCONH—CH$_2$<u>CH</u>$_2$CH$_2$—), 3.24-3.27 (2H, m, —OCONH—<u>CH</u>$_2$CH$_2$CH$_2$—), 3.38 (6H, s, —C<u>H</u>$_3$), 3.40-3.80 (3989H, m, —<u>CH</u>$_2$O(<u>CH</u>$_2$<u>CH</u>$_2$O)$_m$CH$_3$, <u>CH</u>O(<u>CH</u>$_2$<u>CH</u>$_2$O)$_m$CH$_3$, —<u>CH</u>$_2$OCONH_CH$_2$CH$_2$CH$_2$(<u>CH</u>$_2$<u>CH</u>$_2$O)$_n$<u>CH</u>$_2$CH$_2$CH$_2$CH$_2$CH$_2$COOH).

<main peak> number average molecular weight (Mn): 41644, weight average molecular weight (Mw): 42503, polydispersity (Mw/Mn): 1.021, peak top molecular weight (Mp): 43099;

<whole peak> number average molecular weight (Mn): 40285, weight average molecular weight (Mw): 42231, polydispersity (Mw/Mn): 1.048, peak top molecular weight (Mp): 43099.

Low-molecular-weight impurities: 3.02%

Example 9-3

When the compound of the formula (p20) was analyzed on a liquid chromatography using an ion-exchange column (concentration of ammonium formate buffer solution: 0.15 mM), ionic functional group-containing impurities other than the target compound were detected in an amount of 0.15%.

Example 10

Modification of Insulin

Using the succinimide ester compound (p17), insulin (recombinant human insulin, Mw 5800, manufactured by SEROLOGICALS CORPORATION) was modified.

Using 0.1N sodium borate buffer (pH=8.8), 10 mg/ml buffer solution of the insulin was prepared. Into 100 µl of the solution was added 6.9 mg of the compound of the formula (p17), followed by 2 hours of reaction at 4° C. Then, the reaction liquid was diluted into 0.25 µg/nl and 20 µl of the diluted liquid was mixed with 20 µl of a Tris-SDS sample-treating liquid, followed by heating on a boiling water bath for 2 minutes and 30 seconds. Thereafter, 20 µl of the solution was analyzed by sodium dodecyl sulfate-polyacrylamide gel electrophoresis (8-16T %). The staining was carried out by CBB staining.

Figure 4:
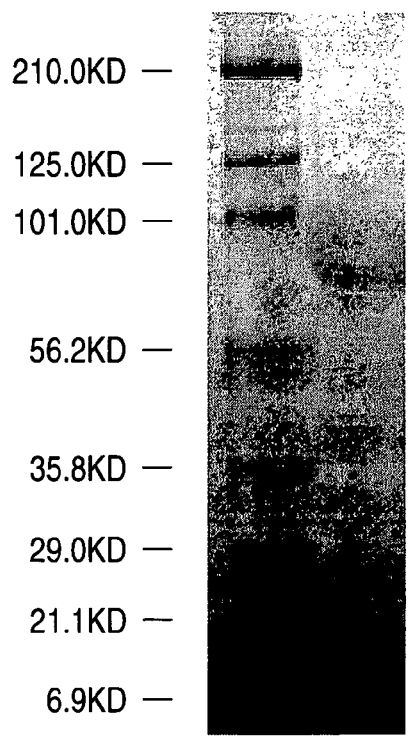
FIG. 4 is a result of electrophoresis of the compounds obtained by modifying insulin with the compound (p17).

The results were shown in FIG. 4. The left lane shows a marker. As a result, it was found that the insulin was modified with the compound of the formula (p17).

What is claimed is:

1. A polyalkylene glycol derivative comprising a compound of the formula (1):

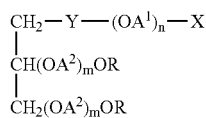     (1)

wherein R is a hydrocarbon group having 1 to 24 carbon atoms, $OA^1$ and $OA^2$ are each an oxyalkylene group having 2 to 4 carbon atoms, the groups represented by R are the same or different from each other in one molecule, the groups represented by $OA^2$ are the same or different from each other in one molecule, m and n each is an average number of moles of the above oxyalkylene group added, m represents 10 to 1000, n represents 1 to 1000, X represents a functional group capable of chemically reacting with a residual group selected from the group selected from the group (I):

Group (I)

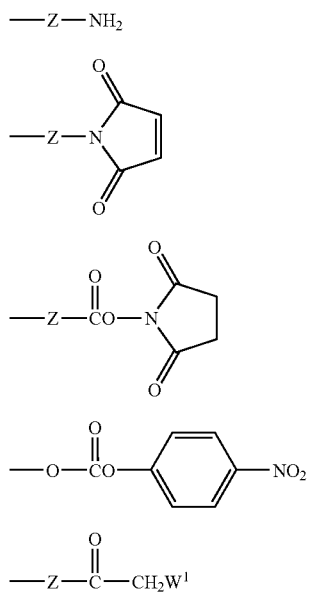

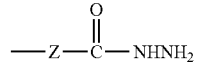     (f)

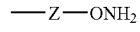     (g)

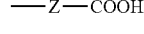     (h)

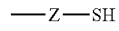     (i)

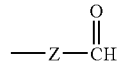     (j)

wherein Z represents an alkylene group alone or an alkylene group containing an ether bond, an ester bond, a urethane bond, an amide bond, a carbonate bond, or a secondary amino group and W' is a halogen atom selected from Cl, Br, and I, and Y is a linker and represents an ether bond, an amide bond, a urethane bond, an ester bond, a secondary amino group, a carbonate bond, or an alkylene group containing these bonds, polydispersity Mw/Mn of the above polyalkylene glycol derivative in gel permeation chromatography satisfying the following relationship:

Mw/Mn<1.08 wherein Mw represents a weight average molecular weight and Mn represents a number average molecular weight.

2. The polyalkylene glycol derivative according to claim 1, which contains low-molecular-weight impurities in an amount of 8% or less in gel permeation chromatography.

3. The polyalkylene glycol derivative according to claim 2, wherein Y is an alkylene group containing an ether bond.

4. The polyalkylene glycol derivative according to claim 3, wherein R is a hydrocarbon group having 1 to 10 carbon atoms, $OA^1$ and $OA^2$ are each an oxyalkylene group having 2 to 3 carbon atoms, n is 1 to 1000, and m is 10 to 1000 in the formula (1).

5. The polyalkylene glycol derivative according to claim 3, wherein R is a methyl group and m is 50 to 1000 in the formula (1).

6. The polyalkylene glycol derivative according to claim 3, wherein X is a group represented by the formula (a):

     (a).

7. The polyalkylene glycol derivative according to claim 6, wherein an amount of impurities containing an ionic functional group other than a target product is 2% or less in a chromatogram obtained by analyzing a polyalkylene glycol derivative represented by the formula (1) by liquid chromatography using an ion-exchange column.

8. The polyalkylene glycol derivative according to claim 3, wherein X is a group represented by the formula (b):

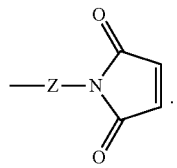
(b)

9. The polyalkylene glycol derivative according to claim 8, wherein an amount of impurities containing an ionic functional group other than a target product is 2% or less in a chromatogram obtained by reacting a polyalkylene glycol derivative represented by the formula (1) with a labeling agent having an ionic functional group and analyzing the resulting product by liquid chromatography using an ion-exchange column.

10. The polyalkylene glycol derivative according to claim 3, wherein X is a group represented by the formula (c):

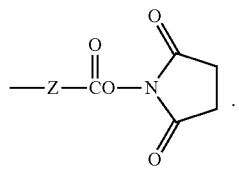
(c)

11. The polyalkylene glycol derivative according to claim 3, wherein X is a group represented by the formula (d):

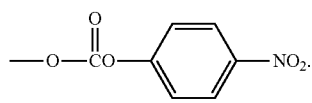
(d)

12. The polyalkylene glycol derivative according to claim 11, wherein an amount of impurities containing an ionic functional group other than a target product is 2% or less in a chromatogram obtained by reacting a polyalkylene glycol derivative represented by the formula (1) with a labeling agent having an ionic functional group and analyzing the resulting product by liquid chromatography using an ion-exchange column.

13. The polyalkylene glycol derivative according to claim 3, wherein X is a group represented by the formula (e):

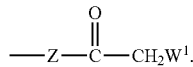
(e)

14. The polyalkylene glycol derivative according to claim 3, wherein X is a group represented by the formula (f):

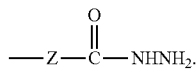
(f)

15. The polyalkylene glycol derivative according to claim 3, wherein X is a group represented by the formula (g):

—Z—ONH$_2$ (g).

16. The polyalkylene glycol derivative according to claim 3, wherein X is a group represented by the formula (h):

—Z—COOH (h).

17. The polyalkylene glycol derivative according to claim 16, wherein an amount of impurities containing an ionic functional group other than a target product is 2% or less in a chromatogram obtained by analyzing a polyalkylene glycol derivative represented by the formula (1) by liquid chromatography using an ion-exchange column.

18. The polyalkylene glycol derivative according to claim 3, wherein X is a group represented by the formula (i):

—Z—SH (i).

19. The polyalkylene glycol derivative according to claim 3, wherein X is a group represented by the formula (j):

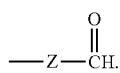
(j)

20. The polyalkylene glycol derivative according to claim 19, wherein an amount of impurities containing an ionic functional group other than a target product is 2% or less in a chromatogram obtained by reacting a polyalkylene glycol derivative represented by the formula (1) with a labeling agent having an ionic functional group and analyzing the resulting product by liquid chromatography using an ion-exchange column.

21. The polyalkylene glycol derivative according to claim 2, wherein Y is selected from an amide bond, a urethane bond, an ester bond, a secondary amino group, a carbonate bond, and an alkylene group containing these bonds in the formula (1).

22. The polyalkylene glycol derivative according to claim 21, wherein R is a hydrocarbon group having 1 to 10 carbon atoms, OA$^1$ and OA$^2$ are each an oxyalkylene group having 2 to 3 carbon atoms in the formula (1).

23. The polyalkylene glycol derivative according to claim 21, wherein R is a methyl group, and m is 50 to 1000 in the formula (1).

24. The polyalkylene glycol derivative according to claim 21, wherein X is a group represented by the formula (a):

—Z—NH$_2$ (a).

25. The polyalkylene glycol derivative according to claim 24, wherein an amount of impurities containing an ionic functional group other than a target product is 2% or less in a chromatogram obtained by analyzing a polyalkylene glycol derivative represented by the formula (1) by liquid chromatography using an ion-exchange column.

26. The polyalkylene glycol derivative according to claim 21, wherein X is a group represented by the formula (b):

(b)

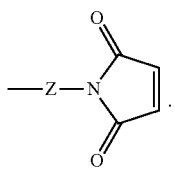

27. The polyalkylene glycol derivative according to claim 26, wherein an amount of impurities containing an ionic functional group other than a target product is 2% or less in a chromatogram obtained by reacting a polyalkylene glycol derivative represented by the formula (1) with a labeling agent having an ionic functional group and analyzing the resulting product by liquid chromatography using an ion-exchange column.

28. The polyalkylene glycol derivative according to claim 21, wherein X is a group represented by the formula (c):

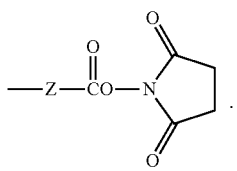
(c)

29. The polyalkylene glycol derivative according to claim 21, wherein X is a group represented by the formula (d):

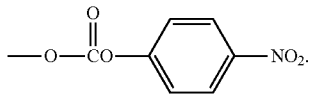
(d)

30. The polyalkylene glycol derivative according to claim 29, wherein an amount of impurities containing an ionic functional group other than a target product is 2% or less in a chromatogram obtained by reacting a polyalkylene glycol derivative represented by the formula (1) with a labeling agent having an ionic functional group and analyzing the resulting product by liquid chromatography using an ion-exchange column.

31. The polyalkylene glycol derivative according to claim 21, wherein X is a group represented by the formula (e):

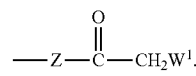
(e)

32. The polyalkylene glycol derivative according to claim 21, wherein X is a group represented by the formula (f):

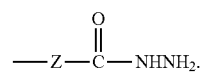
(f)

33. The polyalkylene glycol derivative according to claim 21, wherein X is a group represented by the formula (g):

(g).

34. The polyalkylene glycol derivative according to claim 21, wherein X is a group represented by the formula (h):

(h).

35. The polyalkylene glycol derivative according to claim 34, wherein an amount of impurities containing an ionic functional group other than a target product is 2% or less in a chromatogram obtained by analyzing a polyalkylene glycol derivative represented by the formula (1) by liquid chromatography using an ion-exchange column.

36. The polyalkylene glycol derivative according to claim 21, wherein X is a group represented by the formula (i):

(i).

37. The polyalkylene glycol derivative according to claim 21, wherein X is a group represented by the formula (j):

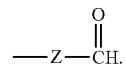
(j)

38. The polyalkylene glycol derivative according to claim 37, wherein an amount of impurities containing an ionic functional group other than a target product is 2% or less in a chromatogram obtained by reacting a polyalkylene glycol derivative represented by the formula (1) with a labeling agent having an ionic functional group and analyzing the resulting product by liquid chromatography using an ion-exchange column.

39. The polyalkylene glycol derivative according to claim 1, wherein R is a hydrocarbon group having 1 to 24 carbon atoms selected from the group consisting of an alkyl group, an alkenyl group, an alkynyl group and an aryl group.

* * * * *